United States Patent

Lee et al.

[11] Patent Number: 5,332,811
[45] Date of Patent: Jul. 26, 1994

[54] ETOPSIDE ANALOGS

[75] Inventors: Kuo-Hsiung Lee, Chapel Hill; Xiao-Ming Zhou, Carrboro; Zhe-Qing Wang, Durham, all of N.C.; Jang-Yang Chang, North Haven, Conn.; Hong-Xing Chen, New Haven, Conn.; Yung-Chi Cheng, Woodbridge, Conn.; Ya-Ching Shen, San Diego, Calif.; Fu-Shen Han, New Haven, Conn.; Hong Hu; Yi-Lin Zhang, both of Chapel Hill, N.C.

[73] Assignee: The University of North Carolina at Chapel Hill, Chapel Hill, N.C.

[21] Appl. No.: 693,300

[22] Filed: May 1, 1991

Related U.S. Application Data

[63] Continuation-in-part of Ser. No. 406,330, Sep. 12, 1989, Pat. No. 5,132,322.

[51] Int. Cl.$^5$ .................. C07D 413/02; C07D 307/77
[52] U.S. Cl. ................................ 544/148; 544/378; 546/174; 546/197; 546/270; 549/298
[58] Field of Search .................. 549/298; 514/232.5, 514/253, 338, 463, 468; 544/148, 378; 546/174, 197, 270

[56] References Cited

U.S. PATENT DOCUMENTS 4,788,216 11/1988 Leander et al. .................. 549/298

FOREIGN PATENT DOCUMENTS 63-23884 1/1988 Japan .

OTHER PUBLICATIONS

Wang et al., "J. Med. Chem.", vol. 33, No. 9, pp. 2660–2663, 1990.

Primary Examiner—C. Warren Ivy
Assistant Examiner—Ba K. Trinh
Attorney, Agent, or Firm—Cushman Darby & Cushman

[57] ABSTRACT

Compounds which are analogs of etoposide and which exhibit anti-tumor activity are disclosed. These compounds having the following structure:

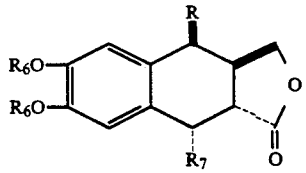

wherein R is selected from

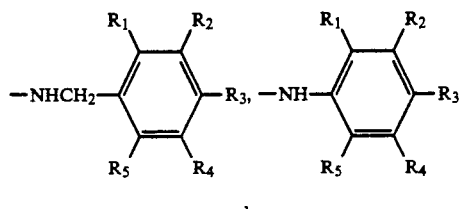

and

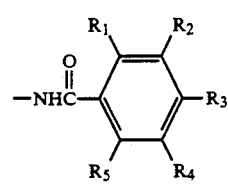

wherein $R_1$, $R_2$, $R_3$, $R_4$ and $R_5$ are each independently selected from H, $CH_3$, $C_2H_5$, $C_3H_7$, i—$C_3H_7$, $C_4H_9$, $CF_3$, $OCH_3$, $OC_2H_5$, $OC_3H_7$, $OC_4H_9$, O—i—$C_3H_7$, O—i—$C_4H_9$, —$OCH_2O$—, —$OCH_2CH_2O$—, $CH_2OH$, $C_2H_4OH$, $CH_2Cl$ $C_2H_4Cl$, $CH_2F$, $C_2H_4F$, $CH_2OCH_3$, $COCH_3$, $COC_2H_5$, $CO_2CH_3$, $CO_2C_2H_5$, $NO_2$, $NH_2$, $NH_2.HCl$, $NH_2.HAc$, $NH_2.1/2H_2SO_4$, $NH_2.1/3H_3PO_4$, $N(CH_3)_2$, $N(C_2H_5)_2$, OH, CN, $N_3$, $SO_2H$, $SO_2NH_2$, $SO_2Cl$, phenyl, substituted phenyl, phenoxy, substituted phenoxy, anilinyl, substituted anilinyl, cyclohexyl, piperidine, (Abstract continued on next page.)

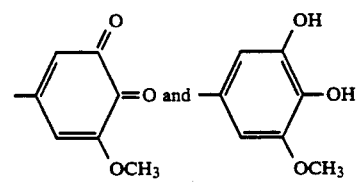
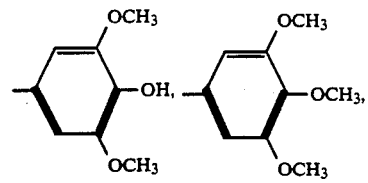
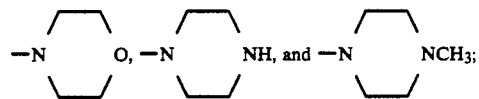
wherein $R_6$ is selected from hydrogen, methyl, ethyl, n-propyl, i-propyl, butyl and bridged methylene;
wherein $R_7$ is selected from
4 Claims, No Drawings

ETOPSIDE ANALOGS

This application is a continuation in part of application No. 07/406,330, filed Sep. 12, 1989 now U.S. Pat. No. 5,132,322.

FIELD OF THE INVENTION

The present invention relates to compounds which are analogs of etoposide. These compounds possess antitumor activity. This invention also relates to a method for treating tumors by administering a safe and effective amount of the etoposide analog compounds.

BACKGROUND OF THE INVENTION

Podophyllotoxin is a naturally occurring compound extracted from the mandrake plant. Recently a therapeutically useful semi-synthetic glycoside of podophyllotoxin, etoposide (also known as VP-16), shown below, has been developed.

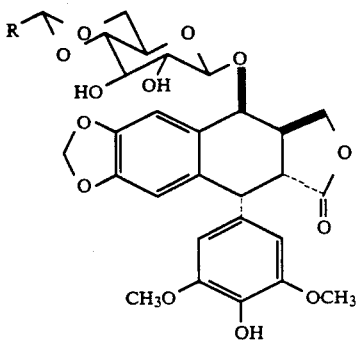

R = CH$_3$

This compound exhibits therapeutic activity in several human neoplasms, including small cell carcinomas of the lung, testicular carcinomas, Hodgkin's disease, leukemia, lymphoma and Kaposi's Sarcoma.

It is believed that these drugs block the catalytic activity of DNA topoisomerase II by stabilizing an enzyme-DNA complex in which the DNA is cleaved and covalently linked to the enzyme. See Chen, G. L., Yang, L., Rowe T. C., Halligan, B. D., Tewey, K., and Liu, L., *J. Biol. Chem.*, 259, 13560 (1984); Ross, W., Rowe, T., Glisson, B., Yalowich, J., and Liu, L., *Cancer Res.*, 44, 5857 (1984); Rowe, T., Kuppfer, G., and Ross, W., *Biochem. Pharmacol.*, 34, 2483 (1985), which are all herein specifically incorporated by reference. By way of background, topoisomerases are enzymes which control the topological state of DNA. Type II topoisomerases catalyze DNA strand passage through transient double strand breaks in the DNA. The resulting change in the linking number of DNA allows these enzymes to mediate DNA interconversions, such as supercoiling and relaxation of supercoiling, catenation and decatenation, knotting, and unknotting. See Wang, J. C., *Annu. Rev. Biochem.*, 54, 665 (1985) and Maxwell, A., and Gellert, M., *Adv. Protein Chem.*, 38, 69 (1986), which are herein specifically incorporated by reference.

Type II DNA topoisomerase enzymes have been shown to be involved in a number of vital cellular processes, including DNA replication and transcription, and chromosomal segregation. These enzymes, therefore, are a critical target for the action of a wide variety of anticancer drugs, including etoposide. The key step leading to cell death may be the capability of these drugs to block the catalytic activity of DNA topoisomerase II, as noted above.

Structure-activity studies have demonstrated a direct correlation between cytotoxicity, DNA breakage, and murine-derived topoisomerase II inhibition activities among the podophyllotoxin analogues. See Minocha, A., and Long, B., *Biochem Res. Comm.*, 122, 165 (1984), which is herein specifically incorporated by reference. The isolation and purification of human type II topoisomerase from lymphocytic leukemia cells has provided the means to use this enzyme as a target to investigate the structure-activity relationships among etoposide and related congeners.

It has been shown that the substitution of etoposide's glycosidic moiety by an 4-alkoxy group, as in 4'-demethyl-epipodophyllotoxin ethyl ether, preserves the inhibitory activity of DNA topoisomerase II intact at higher concentrations. See Thurston, L.S., Irie, H., Tani, S., Han, F. S., Liu, Z. C., Cheng, Y.C., and Lee, K. H., *J. Med. Chem.*, 29, 1547 (1986), which is herein specifically incorporated by reference. However, it has also been shown that a series of 4-acyl congeners are less active, even though some of them possessed potent cytotoxicity. See Thurston, L. S., Imakura, Y., Haruna, M., Li, D. H., Liu, Z. C./Liu, S. Y., Cheng, Y. C., and Lee, K. H., *J. Med. Chem.*, 31, (1988), which is herein specifically incorporated by reference.

Although etoposide has been widely used at the clinical level, the development of drug resistance, myelosuppression, and poor oral bioavailability has encouraged synthesis of analogs related to etoposide which possess preferred pharmacological profiles. Previous studies by the inventors were directed at substituted amino analogs. These analogs are disclosed in U.S. patent application No. 07/313,826, filed Feb. 23, 1989, hereby incorporated by reference. These compounds are also disclosed in the literature, *J. Med. Chem.*, 33:1364 (1990) and 33:2660 (1990). The compounds described therein have yielded numerous useful compositions which can be converted to water soluble products. Not only are many of these compounds more potent than etoposide in the inhibition of human DNA topoisomerase II and in causing protein linked DNA breakage, but these compounds also display activity against KB resistant cells.

Other etoposide analogs which possess anti-cancer activity have been disclosed in Japanese patent No. H1-197486 (August 9, 1989). The Japanese patent discloses compounds of the following formula:

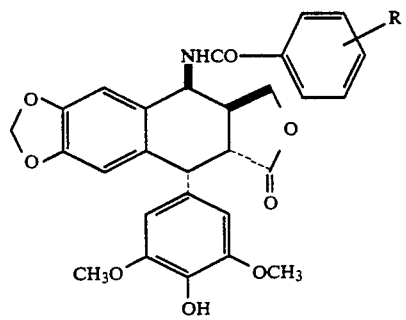

wherein R is a sugar moiety selected from arabinosyl, xyrosyl, hamnosyl, glucosyl, and 4,6-ethylene glucosyl.

This patent also discloses a synthetic method for the intermediate of the formula:

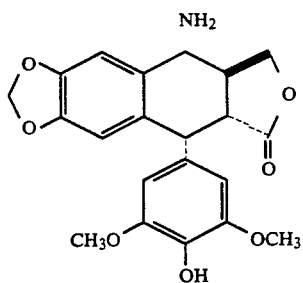

Better methods for the production of this compound have been disclosed by Lee et al. *J. Nat. Prod.*, 52:606-13, May-June 1989. A preferred method for making this compound is also disclosed in Scheme 1 of the present application.

Another podophyllotoxin derivative synthesized in the art is 3',4'-didemethoxy-3',4'-dioxopodophyllotoxin of formula:

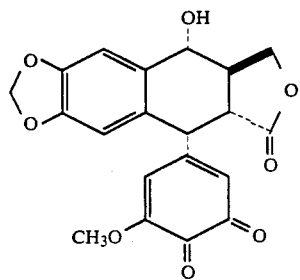

Ayers and Lim disclosed the synthesis of this compound by reacting podophyllotoxin with nitric acid in *Cancer Chemother. Pharmacol.*, 7:99 (1980). Nemec discloses a similar oxidation of Etoposide-3'4'-orthoquinone, and related compounds, in U.S. Pat. No. 4,609,664 using sodium periodate as an oxidizing agent.

SUMMARY OF THE INVENTION

The present invention provides novel etoposide analogs of formula I which exhibit antitumor activity.

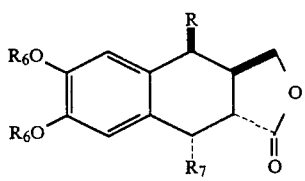

wherein R is selected from

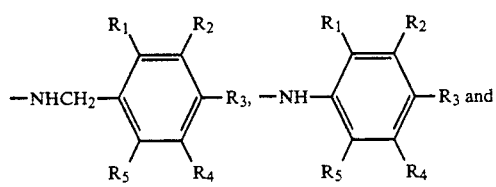

-continued

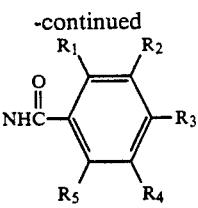

wherein $R_1$, $R_2$, $R_3$, $R_4$ and $R_5$ are each independently selected from H, $CH_3$, $C_2H_5$, $C_3H_7$, i—$C_3H_7$, $C_4H_9$, $CF_3$, $OCH_3$, $OC_2H_5$, $OC_3H_7$, $OC_4H_9$, O—i—$C_3H_7$, O—i—$C_4H_9$, $OCH_2O$, $OCH_2CH_2O$, $CH_2OH$, $C_2H_4OH$, $CH_2Cl$, $C_2H_4Cl$, $CH_2F$, $C_2H_4F$, $CH_2OCH_3$, $COCH_3$, $COC_2H_5$, $CO_2CH_3$, $CO_2C_2H_5$, $NO_2$, $NH_2$, $NH_2.HCl$, $NH_2.HAc$, $NH_2.1/2H_2SO_4$, $NH_2.1/3H_3PO_4$, $N(CH_3)_2$, $N(C_2H_5)_2$, OH, CN, $N_3$, $SO_2H$, $SO_2NH_2$, $SO_2Cl$, phenyl, substituted phenyl, phenoxy, substituted phenoxy, anilinyl, substituted anilinyl, cyclohexyl, piperidine,

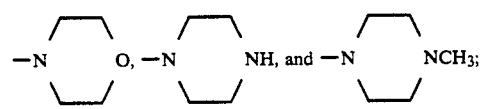

wherein $R_6$ is selected from hydrogen, methyl, ethyl, n-propyl, i-propyl, butyl and bridged methylene; wherein $R_7$ is selected from

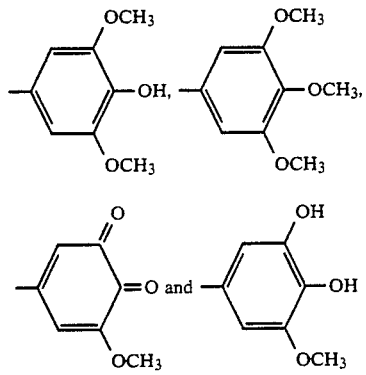

More specifically, preferred compounds of the present invention are etoposide analogs wherein the glycosidic moiety is replaced by substituents which contain aryl groups. The compounds of the present invention have been shown to inhibit type II human topoisomerase and also to cause cellular protein-linked DNA breakage and, therefore, may be useful in the treatment of tumors. The compounds may also be useful in the treatment of papilloma virus.

Another aspect of the present invention is the use of the claimed compounds to treat tumors. A further aspect of the claimed invention is pharmaceutical compositions which contain the compounds of the present invention along with a pharmaceutically acceptable carrier.

A further aspect of the present invention is a process for synthesizing the compounds of the present invention.

Additional objects and advantages of the invention will be set forth in part in the description which follows, and in part will be obvious from the description, or may be learned from the practice of the invention.

DESCRIPTION OF THE PREFERRED EMBODIMENTS

Reference will now be made in detail to the preferred embodiments of the present invention, which together with the following examples, serve to explain the principles of the invention.

One aspect of the present invention is a group of compounds of formula II:

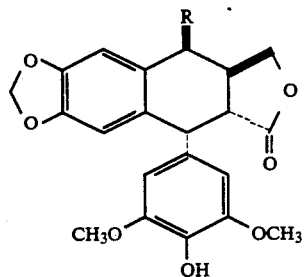

wherein R is

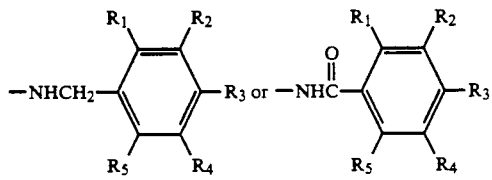

wherein $R_1$, $R_2$, $R_3$, $R_4$ and $R_5$ are each independently selected from H, $CH_3$, $C_2H_5$, $C_3H_7$, i—$C_3H_7$, $C_4H_9$, $CF_3$, $OCH_3$, $OC_2H_5$, $OC_3H_7$, $OC_4H_9$, O—i—$C_3H_7$, O—i—$C_4H_9$, $OCH_2O$, $OCH_2CH_2O$, $CH_2OH$, $C_2H$ $_4OH$, $CH_2Cl$ $C_2H_4Cl$, $CH_2F$, $C_2H_4F$, $CH_2OCH_3$, $COCH_3$, $COC_2H_5$, $CO_2CH_3$, $CO_2C_2H_5$, $NO_2$, $NH_2$, $NH_2.HCl$, $NH_2.HAc$, $NH_2.1/2H_2SO_4$, $NH_2.1/3H_3PO_4$, $N(CH_3)_2$, $N(C_2H_5)_2$, OH, CN, $N_3$, $SO_2H$, $SO_2NH_2$, $SO_2Cl$, phenyl, substituted phenyl, phenoxy, substituted phenoxy, anilinyl, substituted anilinyl, cyclohexyl, piperidine,

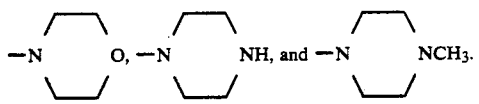

These 4β-substituted benzylamino-4'-O-demethyl podophyllotoxins are a group of derivatives of etoposide which possess anti-cancer activity. It was surprisingly found that the activity of some of these compounds is two to ten times greater than the activity of etoposide. Table 1 illustrates the inhibitory activity of compounds of this type.

Preferred compounds of formula II are those where R is selected from benzylamino, 4"-nitro-benzylamino, 3"-nitrobenzylamino, 2"-nitrobenzylamino, 2"-fluorobenzylamino, 3"-fluorobenzylamino, 4"-fluorobenzylamino, 3"-cyanobenzylamino, 4"-cyanobenzylamino, 3",5"-dimethoxybenzylamino, 3"-aminobenzylamino, 2"-aminobenzylamino, benzoylamino, 2"-hydroxybenzoylamino, 4"-fluorobenzoylamino, 4"-acetoxybenzoylamino, 4"-acetylbenzoylamino, 3"-cyanobenzoylamino, 4"-cyanobenzoylamino, 3"-nitrobenzoylamino and 3"-aminobenzoylamino. Particularly preferred compounds of formula II are those where R is selected from 3"-fluorobenzylamino, 3"-cyanobenzylamino and 4"-cyanobenzylamino. The particularly preferred compounds demonstrate over twice the inhibition of DNA topoisomerase activity as etoposide and over twice the inhibition of cellular protein-DNA complex formation. The inhibition data for compounds of formula II is shown in tables 1 and 4.

Compounds of formula II are produced by the synthetic method disclosed in scheme 1. unlike the prior processes, which involved a difficult separation of the key intermediate (3) from its 4α-amino isomer (J. Natl Prod, 52:606 (1989); Japan Pat. HI197486). The process shown in scheme I allows the formation of the presently disclosed compounds by production of the β-isomer. This eliminates the need for the difficult separation disclosed previously.

Another aspect of the present invention is a group of compounds of formula III:

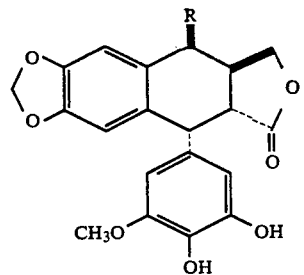

wherein R is

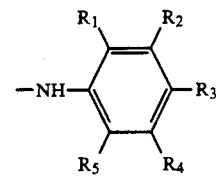

wherein $R_1$, $R_2$, $R_3$, $R_4$ and $R_5$ are each independently selected from H, $CH_3$, $C_2H_5$, $C_3H_7$, i—$C_3H_7$, $C_4H_9$, $CF_3$, $OCH_3$, $OC_2H_5$, $OC_3H_7$, $OC_4H_9$, O—i—$C_3H_7$, O—i—$C_4H_9$, $OCH_2O$, $OCH_2CH_2O$, $CH_2OH$, $C_2H$ $_4OH$, $CH_2Cl$ $C_2H_4Cl$, $CH_2F$, $C_2H_4F$, $CH_2OCH_3$, $COCH_3$, $COC_2H_5$, $CO_2CH_3$, $CO_2C_2H_5$, $NO_2$, $NH_2$, $NH_2.HCl$, $NH_2.HAc$, $NH_2.1/2H_2SO_4$, $NH_2.1/3H_3PO_4$, $N(CH_3)_2$, $N(C_2H_5)_2$, OH, CN, $N_3$, $SO_2H$, $SO_2NH_2$, $SO_2Cl$, phenyl, substituted phenyl, phenoxy, substituted phenoxy, anilinyl, substituted anilinyl, cyclohexyl, piperidine,

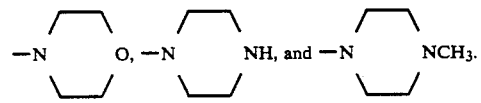

These 4β-substituted anilinyl-3',4'-O-didemethyl podophyllotoxins are another group of derivatives of etoposide which possess anti-cancer activity. The activity of some of the preferred compounds of this type is surprisingly greater then that of etoposide itself. Table 2 illustrates the inhibitory activity of compounds of this type.

Preferred compounds of formula III are those where R is selected from anilino, 4″-fluoroanilino, 3″-hydroxyanilino, 4″-cyanoanilino, 4″-nitroanilino, 3″-methoxycarbonylanilino, and 3″,4″-0-methylenedioxyanilino. A particularly preferred compound of formula III is a compound where R is selected from 4″-nitroanilino. This particularly preferred compound demonstrates over twice the inhibition of DNA topoisomerase activity as etoposide and over twice the inhibition of cellular protein-DNA complex formation.

Compounds of formula III are produced by the synthetic method disclosed in scheme 2. Ayres and Lim, in *Cancer Chemother. Pharmacol.*, 1982, 7:99, disclosed the synthesis of 3',4'-dioxo-3',4'-didemethoxy podophyllotoxin of the following structure.

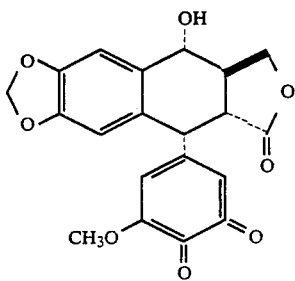

The enantiomer of this structure is used as an intermediate in the synthesis of the compounds of formula III. It is then reacted as shown in scheme 2 to produce the compounds of formula III.

A further aspect of the present invention are compounds of formula IV.

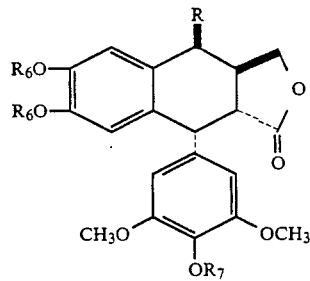

wherein R is

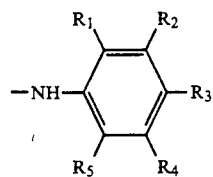

wherein $R_1$, $R_2$, $R_3$, $R_4$ and $R_5$ are each independently selected from H, $CH_3$, $C_2H_5$, $C_3H_7$, i—$C_3H_7$, $C_4H_9$, $CF_3$, $OCH_3$, $OC_2H_5$, $OC_3H_7$, $OC_4H_9$, O—i—$C_3H_7$, O—i—$C_4H_9$, $OCH_2O$, $OCH_2CH_2O$, $CH_2OH$, $C_2H_4OH$, $CH_2Cl$ $C_2H_4Cl$, $CH_2F$, $C_2H_4F$, $CH_2OCH_3$, $COCH_3$, $COC_2H_5$, $CO_2CH_3$, $CO_2C_2H_5$, $NO_2$, $NH_2$, $NH_2.HCl$, $NH_2.HAc$, $NH_2.1/2H_2SO_4$, $NH_2.1/3H_3PO_4$, $N(CH_3)_2$, $N(C_2H_5)_2$, OH, CN, $N_3$, $SO_2H$, $SO_2NH_2$, $SO_2Cl$, phenyl, substituted phenyl, phenoxy, substituted phenoxy, anilinyl, substituted anilinyl, cyclohexyl, piperidine,

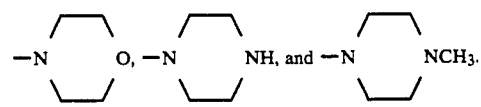

wherein $R_6$ is selected from H, $CH_3$, $C_2H_5$, $C_3H_7$, i—$C_3H_7$, and $C_4H_9$ and wherein $R_7$ is H or $CH_3$.

Preferred compounds of formula IV are those where R is selected from anilino, 4″-nitroanilino, 4″-ethoxycarbonylanilino, 4″-cyanoanilino, 4″-fluoroanilino, and 3″-hydroxyanilino; $R_6$ is hydrogen, and $R_7$ is selected from methyl and hydrogen. The results of DNA inhibition assays of DNA topoisomerase and of cellular protein-DNA complex formation inhibition, for these compounds, are shown in Table 3.

The synthesis of compounds of formula IV is shown in scheme 3. Schrier, in *Helv. Chim. Acta.*, 47:1529 (1964) disclosed the synthesis of 6,7-0-dimethyl-6,7-0-demethylenepodophylotoxin, shown below.

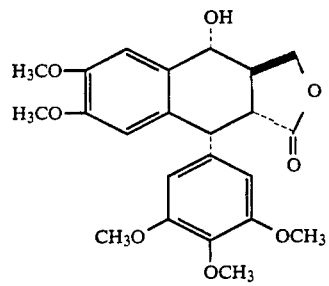

The related 6,7-dihydroxycompound serves as the intermediate in the synthesis of the compounds of formula IV, as seen in scheme 3.

Still another aspect of the present invention is compounds of formula V.

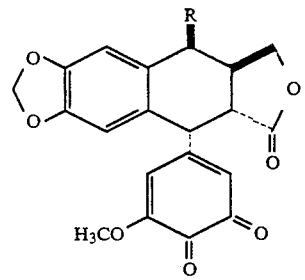

wherein R is

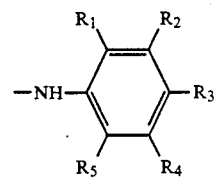

wherein $R_1$, $R_2$, $R_3$, $R_4$ and $R_5$ are each independently selected from H, $CH_3$, $C_2H_5$, $C_3H_7$, i—$C_3H_7$, $C_4H_9$, $CF_3$, $OCH_3$, $OC_2H_5$, $OC_3H_7$, $OC_4H_9$, O—i—

—$C_3H_7$, $O-i-C_4H_9$, $OCH_2O$, $OCH_2CH_2O$, $CH_2OH$, $C_2H_4OH$, $CH_2Cl$, $C_2H_4Cl$, $CH_2F$, $C_2H_4F$, $CH_2OCH_3$, $COCH_3$, $COC_2H_5$, $CO_2CH_3$, $CO_2C_2H_5$, $NO_2$, $NH_2$, $NH_2.HCl$, $NH_2.HAc$, $NH_2.1/2H_2SO_4$, $NH_2.1/3H_3PO_4$, $N(CH_3)_2$, $N(C_2H_5)_2$, OH, CN, $N_3$, $SO_2H$, $SO_2NH_2$, $SO_2Cl$, phenyl, substituted phenyl, phenoxy, substituted phenoxy, anilinyl, substituted anilinyl, cyclohexyl, piperidine,

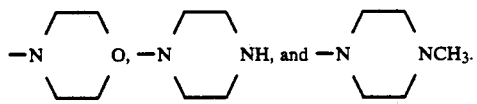

Preferred compounds of formula V are those where R is selected from 4″-fluoroanilino, 4″-nitroanilino and 4″-ethoxycarbonylanilino. Results of the inhibition tests for these compounds are shown in table 5.

These modifications will produce changes in inhibitory activity which can be readily determined by assays known in the prior art through the exercise of routine skill in light of the teachings contained herein.

The compounds of the present invention were tested for their degree of inhibitory activity on human type II DNA topoisomerase, their effect on the formation of protein-linked DNA breakage, and their cytotoxicity. The inhibitory activity for compounds of the present invention correlated with the ability of the compounds to cause DNA strand breakage. However, the in vitro cytotoxicity of the compounds tested did not appear to correlate with the enzyme inhibitory activity and DNA strand break activity. The results of the tests on some of the compounds of the present invention are shown in Tables 1 to 5. For a description of the assays used with respect to the compounds listed in Tables 1 to 5 see Thurston, L.S., Irie, H., Tani, S., Han, F. S., Liu, Z. C., Cheng, Y.C., and Lee, K. H., Antitumor Agents 78. Inhibition of Human DNA Topoisomerase II by Podophyllotoxin and Peltatin Analogues, J. Med. Chem. 29, 1547 (1986), and the references cited therein, herein incorporated by reference.

Tables 1 to 5 illustrate the inhibitory activity, DNA strand breakage ability, as well as the cytotoxicity of etoposide and some of the compounds of the present invention.

Preparation of compounds within the scope of the present invention appear in the following examples.

EXAMPLE 1

4′-O-Demethyl-4β-azido-4-desoxypodophyllotoxin (1)

To 1.60 g (4.00 mmol) of 4′-O-Demethylepipodophyllotoxin (3) and 1.32 g (20.00 mmol) of sodium azide in 8 ml of $CHCl_3$ was added 4 ml trifluoroacetic acid (5.19 mmol) dropwise. The reaction mixture was stirred for 15 min. Saturated aqueous sodium bicarbonate solution was added. The organic layer was washed with water and dried over $MgSO_4$. After the solvent was removed, the crude produce was purified by column chromatography (silica gel 100 g, chloroform:acetone:ethyl acetate = 100:5:5) to give 1.5 g of product (94%): mp 215°–217° C., crystals from chloroform and ethyl acetate; $^1$H-NMR ($CDCl_3$) 6.82 (s, 1H, 5-H), 6.60 (s, 1H, 8-H), 6.28 (s, 2H, 2′,6′-H), 6.04 (s, 1H, OCHO), 6.02 (s, 1H, OCHO), 5.43 (s, 1H, OH), 4.78 (d, 1H, J=3.7Hz, 1-H), 4.64 (d, 1H, J=5.2Hz, 4-H), 4.32 (d, 2H, J=9.2Hz, 11-$H_2$), 3.79 (2, 6H, 3′,5′-$OCH_3$), 3.18 (dd, 1H, J=5.1$H_2$, 2-H) and 2.95 (m, 1H, 3-H); IR (KBr) 3400, 2920, 2100, 1720, 1602, and 1460 cm$^{-1}$.

EXAMPLE 2

4′-O-Demethyl-4β-amino-4-desoxypodophyllotoxin (2)

To a solution of 4 (1.5 g, 3.53 mmol) in 80 ml of ethyl acetate was added 300 mg of 10% palladium on active carbon. The mixture was stirred overnight under hydrogen. The reaction mixture was filtered and the filtrate was evaporated. The crude product was purified by column chromatography (silica gel 80 g, $CHCl_3$:EtOAc=2:1 and $CHCl_3$:EtOAc:-MeOH=2:1:0.1) to give 1.18 of 5 (70%). The spectral data, specific rotation, and melting point of 5 are consistent with those reported (J. Natl. Prod., 1989, 52:606)

GENERAL PROCEDURE FOR THE SYNTHESIS OF EXAMPLES 3 TO 12

To a solution of substituted benzyl bromide (0.79 mmol) in acetone (3 ml) was added sodium iodide (128 mg, 0.85 mmol). The reaction mixture was stirred for 20 min and then filtered. The filtrate was evaporated to give the corresponding benzyl iodide. To compound 2 in 1,2-dichloroethane (4 ml) was added the substituted benzyl iodide (0.79 mmol) and the anhydrous barium carbonate (0.95 mmol) under nitrogen. After the mixture was stirred for 40 h at 75°–80° C., it was filtered and the organic solvent was removed. The crude product was purified by column chromatography ($CHCl_3$:$CH_3COCH_3$:EtOAc=100:5:5).

EXAMPLE 3

4′-O-Demethyl-4β-benzylamino-4-desoxypodophyllotoxin:

Yield 54%; mp 180°–181° C.; crystals from chloroformethyl acetate; $[\alpha]_D^{25}$ −65° (c=0.25, $CHCl_3$); $^1$H NMR ($CDCl_3$) 7.37 (m, 5H, 2″, 3″, 4″, 5″, 6″-H), 6.54 (s, 1H, 5-H), 6.48 (s, 1H, 8-H), 6.29 (s, 2H, 2′,6′-H), 5.96 (s, 1H, OCHO), 5.94 (s, 1H, OCHO), 5.40 (s, 1H, OH), 4.54 (d, 1H, J=5.1 Hz, 1-H), 4.32 (m, 2H, 11-$H_2$), 3.94 (d, 1H, J=3.8 Hz, 4-H), 3.89 (d, 2H, J=2.7 Hz, $NCH_2$), 3.78 (s, 6H, 3′5′-$OCH_3$), 3.34 (dd, 1H, J=, 14.0, 5.2Hz, 2-H) and 2.82 (m,. 1H, 3-H); IR (KBr) 3300, 2850, 1760, 1590 and 1490 cm$^{-1}$.

EXAMPLE 4

4′-O-Demethyl-4β-(4″-nitrobenzylamino)-4-desoxypodophyllotoxin

Yield 48%; mp 216°–217° C.; crystals from chloroformethyl acetate; $[\alpha]_D^{25}$ −61° (c=0.25, $CHCl_3$); $^1$H NMR (CDCL$_3$) δ 8.23 (d, 2H, J=8.5Hz, 3″,5″-H), 7.55 (d, 2H, J=8.5Hz, 2″,6″-H), 6.67 (s, 1H, 5-H), 6.52 (s, 1H, 8-H), 6.30 (s, 2H, 2′,6′-H), 5.99 (s, 1H, OCHO), 5.95 (s, 1H, OCHO), 5.41 (s, 1H, OH), 4.57 (d, 1H, J=5.2Hz, 1-H), 4.29 (m, 2H, 11-$H_2$), 4.16 (d, 1H, J=14.3 Hz, NCH), 3.96 (d, 1H, J=3.9Hz, 4-H), 3.91 (d, 1H, J=14.3Hz, NCH), 3.75 (s, 6H, 3′,5′-$OCH_3$), 3.32 (dd, 1H, J=, 14.0, 5.2Hz, 2-H) and 2.86 (m, 1H, 3-H); IR (KBr) 3380, 2890, 1750, 1600, 1515, 1470, 1470 and 1330 cm$^{-1}$.

EXAMPLE 5

4′-O-Demethyl-4β-(3″-nitrobenzylamino)-4-desoxypodophyllotoxin

Yield 45%; mp 196°–198° C.; crystals from chloroformethyl acetate; $[\alpha]_D^{25}$ −67° (c=0.25, $CHCl_3$); $^1$H NMR ($CDCl_3$) δ 8.19 (s, 1H, 2″-H), 8.14 (d, 1H, J=8.0Hz, 4''-H), 7.70 (d, 1H, J=7.6Hz, 6''-H), 7.53 (t, 1H, J=8.0Hz, 5''-H), 6.63 (s, 1H, 5-H), 6.48 (s, 1H, 8-H), 6.26 (s, 2H, 2',6'-H), 5.99 (s, 1H, OCHO), 5.95 (s, 1H OCHO), 5.38 (s, 1H, OH), 4.54 (d, 1H, J=5.1 Hz, 1-H), 4.30 (m, 2H, 11-H$_2$), 4.12 (d, 1H, J=13.7 Hz, NCH), 3.94 (d, 1H, J=3.9Hz, 4-H), 3.88 (d, 1H, J=13.7 Hz, NCH), 3.75 (s, 6H, 3',5'-OCH$_3$), 3.28 (dd, 1H, J=14.0, 5.3Hz, 2-H) and 2.84 (m, 1H, 3-H); IR (KBr) 3360, 2900, 1760, 1610, 1470, 1520 and 130 cm$^{-1}$. Anal. Calcd for C$_{28}$H$_{26}$N$_2$O$_9$; C, 62.92; H, 4.87; N, 5.24; found c, 62.65; H, 4.85; N. 5.19.

EXAMPLE 6

4'-O-Demethyl-4β-(2''-nitrobenzylamino)-4-desoxypodophyllotoxin

Yield 42%; mp 246°247° C.; crystals from chloroformethyl acetate; [α]$_D^{25}$ −46° (c=)0.25, CHCl$_3$); $^1$H NMR (CDCl$_3$) δ8.02 (d, 1H, J=)8.0Hz, 3''-H), 7.61 (m, 2H, 4'',6''-H), 7.50 (t, 1H, J=8.2Hz, 5''-H), 6.64 (s, 1H, 5-H), 6.49 (s, 1H, 8-H), 6.29 (s, 2H, 2',6'-H), 5.96 (s, 1H, OCHO), 5.93 (s, 1H, OCHO), 5.41 (s, 1H, OH), 4.55 (d, 1H, J=5.2Hz, 1-H), 4.42–4.27 (m, 3H, 11-H$_2$ and NCH), 4.02 (m, 2H, 4-H, NCH), 3.78 (s, 6H, 3',5'-OCH$_3$), 3.31 (dd, 1H, J=14.0, 5.2 Hz, 2-H) and 2.88 (m, 1H, 3-H); IR (KBr) 3380, 2880, 1740, 1600, 1470, 1500 and 1330 cm$^{-1}$. Anal. Calcd for C$_{28}$H$_{26}$N$_2$O$_9$; C, 62.92; H, 4.87; N, 5.24; found C. 62.85; H, 4.91; N, 5.19.

EXAMPLE 7

4-O-Demethyl-4β-(2''-fluorobenzylamino)-4-desoxypodophyllotoxin

Yield 46%; mp 174°–175° C.; crystals from chloroform-ethyl acetate; [α]$_D^{25}$ −66° (c=0.25, CHCl$_3$); $^1$H NMR (CDCl$_3$) δ 7.36 (m, 2H, 4'',5''-H), 7.18 (m, 2H, 3'',5''-H), 6.47 (s, 1H, 5-H), 6.44 (s, 1H, 8-H), 6.28 (s, 2H, 2',6'-H), 5.94 (s, 2H, OCH$_2$O), 5.40 (s, 1H, OH), 4.53 (d, 1H, J=5.2 Hz, 4-H), 4.35 (d, 2H, J=5.2 Hz, 1-H), 4.35 (d, 2H, J=9.2 Hz, 11-H$_2$), 3.81 (m, 3H, 4-H and NCH$_2$), 3.78 (s, 6H, 3',5'-OCH$_3$), 3.34 (dd, 1H, J=14.0, 5.2 Hz, 2-H) and 2.83 (m, 1H, 3-H); IR (KBr) 3350, 2900, 1755, 1600, 1500 and 1475 cm$^{-1}$. Anal. Calcd. for C$_{28}$H$_{26}$NFO$_7$; C. 66.27; H. 5.13; N. 2.76. Found: C. 65.90; H. 5.11; N. 2.84

EXAMPLE 8

4-O-Dimethyl-4β-(3''-fluorobenzylamino)-4-desoxypodophyllotoxin

Yield 51%; mp 154°–155° C.; crystals from ethyl acetate-hexane; [α]$_D^{25}$ −66 (c=0.25, CHCl$_3$); $^1$H NMR (CDCl$_3$) δ 7.31 (m, 1H, 5''-H), 7.13–6.85 (m, 3H, 2'',4' and 6''-H), 6.59 (s, 1H, 5-H), 6.49 (s, 1H, 8-H), 6.24 (s, 2H, 2',6'-H), 5.99 (s, 1H, OCHO), 5.95 (s, 1H, OCHO), 5.40 (s, 1H, OH), 4.55 (d, 1H, J=5.2 Hz, 1-H), 4.34 (m, 2H, 11-H$_2$), 3.85 (m, 3H, 4-H and NCH$_2$), 3.78 (s, 6H, 3',5'-OCH$_3$), 3.34 (dd, 1H, J=14.0, 5.3 Hz, 2-H) and 2.83 (m, 1H, 3-H); IR (KBr) 3390, 2905, 1760, 1610, 1520 and 1480 cm$^{-1}$. Anal. Calcd. for C$_{28}$H$_{26}$NFO$_7$; C. 66.27; H. 5.13; N. 2.76. Found: C. 66.12; H.5.21; N. 2.71.

EXAMPLE 9

4'-O-Demethyl-4β-(4''-fluorobenzylamino)-4-desoxypodophyllotoxin

Yield 45%; mp 148°–150° C.; crystals from ethyl acetate-hexanes; [α]$_D^{25}$ −65° (c=0.25, CHCl$_3$); $^1$H NMR (CDCl$_3$) δ 7.33 (m, 2H, 2'',6''-H), 7.09 (m, 2H, 3'',5''-H), 6.59 (s, 1H, 5-H), 6.49 (s, 1H, 8-H), 6.29 (s, 2H, 2',6'-H), 5.98 (s, 1H, OCHO), 3.94 (s, 1H, OCHO), 5.40 (s, 1H, OH), 4.54 (d, 1H, J=5.3 Hz, 1-H), 4.34 (m, 2H, 11-H$_2$), 3.90 (m, 2H, 4-H and NCH), 3.78 (m, 7H, 3',5'-OCH3 and NCH), 3.32 (dd, 1H, J=14.0, 5.2 Hz, 2-H), 2.85 (m, 1H, 3-H); IR (KBr) 3330, 2880, 1750, 1630, 1500 and 1480 cm$^{-1}$. Anal. Calcd. for C$_{28}$H$_{26}$NFO$_7$; C.66.27; H. 5.13; N. 2.76. Found. C. 66.09; H. 5.16; N. 2.74.

EXAMPLE 10

4'-O-Demethyl-4β-(3''-cyanobenzylamino)-4-desoxypodophyllotoxin

Yield 49%; mp 176°–178° C.; crystals from chloroform-ethyl acetate; [α]$_D^{25}$ −66° (c=0.25, CHCl$_3$); $^1$H NMR (CDCl$_3$) δ 7.61 (m, 3H, 2'',4'' and 6''-H), 7.48 (t, 1H, 5''-H), 6.62 (s, 1H, 5-H), 6.56 (s, 1H, 8-H), 6.28 (s, 2H, 2',6'-H), 5.97 (s, 1H, OCHO), 5.93 (s, 1H, OCHO), 5.41 (s, 1H, OH), 4.55 (d, 1H, J=5.1 Hz, 1-H), 4.26 (m, 2H, 11-H$_2$), 3.88 (m, 3H, 4-H and NCH$_2$), 3.71 (s, 6H, 3',5'-OCH$_3$), 3.30 (dd, J=14.0, 5.2 Hz, 2-H) and 2.84 (m, 1H, 3-H); IR (KBr) 3360, 2900, 2220, 1755, 1600, 1500 and 1480 cm$^{-1}$.

EXAMPLE 11

4'-O-Demethyl-4β-(4''-cyanobenzylamino)-4-desoxypodophyllotoxin

Yield 51%; mp 178°–180° C.; crystals from chloroform-ethyl acetate; [α]$_D^{25}$ −64° (c=0.25, CHCl$_3$); $^1$H NMR (CDCl$_3$) δ 7.65 (d, 2H, J=8.1 Hz, 3'',5''-H), 7.48 (d, 2H, J=8.1 Hz, 2''6''-H), 7.26 (s, 2H, 2',6'-H), 6.64 (s, 1H, 5-H), 6.50 (s, 1H, 8-H), 5.95 (ABq, 2H, J=1.2 Hz, OCH$_2$O), 5.40 (s, 1H, OH), 4.55 (d, 1H, J=5.2 Hz, 1-H), 4.31 (m, 2H, 11-H$_2$), 4.08 (d, 1H, J=14.0 Hz, NCH), 3.93 (d, 1H, J=3.9 Hz, 4-H), 3.86 (d, 1H, J=14.0 Hz, NCH), 3.75 (s, 6H, 3',5'-OCH$_3$), 3.30 (dd, 1H, J=14.0, 5.2 Hz, 2-H) and 2.84 (m, 1H, 3-H); IR (KBr) 3360, 2900, 2220, 1750, 1600, 1500 and 1450 cm$^{-1}$. Anal. Calcd. for C$_{29}$H$_{26}$N$_2$O$_7$; C.67.70; H. 5.05; N. 5.44. Found C. 67.54; H. 5.11; N. 5.40

EXAMPLE 12

4'-O-Demethyl-4β-(3'',5''-dimethoxybenzylamino)-4-desoxypodophyllotoxin

Yield 57%; mp 186°–187° C.; crystals from chloroform-ethyl acetate; [α]$_D^{25}$ −65° (c=0.25, CHCl$_3$); 1H NMR (CDCl$_3$) δ 6.59 (s, 1H, 5-H), 6.51 (d, 2H, J=2.2 Hz, 2'', 6''-H), 6.47 (s, 1H, 8-H), 6.41 (t, 1H, J=2.2 Hz, 4''-H), 6.28 (s, 2H, 2', 6'-H), 5.96 (s, 1H, OCHO), 5.92, (s, 1H, OCHO), 5.40 (s, 1H, OH), 4.54 (d, 1H, J=5.2 Hz, 1-H), 4.34 (m, 2H, 11-H$_2$), 3.92 (d, 1H, J=4.0 Hz, 4-H), 3.84 (s, 8H, NCH$_2$ and 2'',6''-OCH$_3$), 3.77 (s, 6H, 2',6'-OCH$_3$), 3.32 (dd, 1H, J=14.0, 5.2 Hz, 2-H) and 2.81 (m, 1H, 3-H); Ir (KBr) 3360, 2920, 1750, 1600, 1510 and 1470 cm$^{-1}$. Anal. Calcd for C$_{30}$H$_{31}$NO$_9$; C. 65.57; H. 5.65; N. 2.55; Found. C. 65.23; H. 5.55; N. 2.49.

EXAMPLE 13

4'-O-Demethyl-4β-(3''-aminobenzylamino)-4-desoxypodophyllotoxin

Tin (II) chloride dihydrate 110 mg (0.5 mmol) was added to 50 mg (0.1 mmol) of 4'-O-demethyl-4β-(3''-nitrobenzylamino)-4-desoxypodophyllotoxin in ethyl acetate (2ml). After the mixture was refluxed under nitrogen for 1 h, the mixture was filtered, diluted with ethyl acetate, washed with water, dried over MgSO$_4$ and evaporated in vacuo. The crude product was purified by column chromatography (CH$_2$Cl$_2$:CH$_3$CO$_2$Et:-

MeOH=100:5:5) to give the title product; yield 75%; mp 209°-210° C.; crystals from ethyl acetate-hexane; $[\alpha]_D^{25}$ −66° (c=0.25, CHCl₃); ¹H NMR (CDCl₃) δ 7.17 (t, 1H, J=7.7 Hz, 5″-H), 6.73 (d, 1H, J=7.7 Hz, 6″-H), 6.68 (s, 1H, 2″-H), 6.64 (d, 1H, J=7.7 Hz, 4″-H), 6.56 (s, 1H, 5-H), 6.47 (s, 1H, 8-H), 6.29 (s, 2H, 2′,6′-H), 5.96 (s, 1H, OCHO), 5.92 (s, 1H, OCHO), 5.40 (s, 1H, OH), 4.53 (d, 1H, J=5.1 Hz, 1-H), 4.33 (m, 2H, 11-H₂), 3.93 (d, 1H, J=3.9 Hz, 4-H), 3.79 (s, 6H, 3′,5′-OCH₃), 3.34 (dd, 1H, J=12.0, 5.2 Hz, 2-H) and 2.80 (m, 1H, 3-H); IR (KBr) 3440, 3360, 2900, 1760, 1660, 1500 and 1480 cm⁻¹.

EXAMPLE 14

4′-O-demethyl-4β-(2″-aminobenzyl)-4-desoxypodophyllotoxin

This compound was prepared from the product of Example 6 in an analogous way as described above for the preparation of the compound of Example 13. Yield 60%; mp 138°-140° C.; crystals from ethyl acetate-hexane; $[\alpha]_D^{25}$ −85° (c=0.25, CHCl₃); ¹H NMR (CDCl₃) δ 7.15 (m, 2H, 3″,5″-H), 6.75 (m, 3H, 4″,6″-H and 5-H), 6.49 (s, 1H, 8-H), 6.27 (s, 2H, 2′,6′-H), 5.98 (s, 1H, OCHO), 5.94 (s, 1H, OCHO), 5.40 (s, 1H, OH), 4.55 (d, 1H, J=5.2 Hz, 1-H), 4.16 (m, 2H, 11-H₂), 3.93 (m, 3H, 4-H and NCH₂), 3.78 (s, 6H, 3′,5′-OCH₃), 3.20 (dd, 1H, J=14.0, 5.2 Hz, 2-H) and 2.84 (m, 1H, 3-H); IR (KBr) 3400, 3344, 2900, 1750, 1600, 1500 and 1470 cm⁻¹. Anal. Calcd for $C_{28}H_{28}N_2O_7$; C. 66.67; H. 5.56; N 5.56. Found. C. 66.32; H. 5.82; N. 5.33.

EXAMPLE 15

3′,4′-Didemethoxyl-3′,4′-dioxoepipodophyllotoxin

A suspension of 4′-demethylepipodophyllotoxin (2.0 g, 5.0 mmol) in glacial acetic acid (25 ml) was cooled at 5° C. To which was added in one portion of a mixture of 90% nitric acid (3.0 ml) and glacial acetic acid (25 ml) precooled to 5° C. The mixture was stirred for 5 min and then poured into ice-water (500 ml). The precipitate was extracted by chloroform, and the combined organic layers were washed with brine until pH=5-6, dried (Na₂SO₄), and evaporated to give the product (1.24 g 65%) after recrystallization from hexane-ethyl acetate: mp 245°-248° C.; ¹H NMR (CDCl₃) δ 6.83 (s, 1H, 5-H), 6.55 (s, 1H, 8-H), 6.54 (s, 1H, 6′-H), 6.02 (s, 2H, OCH₂O), 5.21 (s, 1H, 2-H), 4.83 (d, J=3.4 Hz, 1H, 11-H), 4.52 (d, H=1.3 Hz, 1H, 4-H), 4.50 (d, J=3.4 Hz, 1H, 11-H), 4.30 (d, J=6.5 Hz, 1H, 1-H), 3.86 (s, 3H. 5′-OCH₃), 3.50 (dd, J=14.1, 5.6 Hz, 1H, 2-H), and 2.83 (m, 1H, 3-H); and IR (KBr) 3480, 2920, 1768, 1695, 1660, 1626, 1560, and 1485 cm⁻¹.

EXAMPLE 16

3′,4′-O-Didemethylepipodophyllotoxin

A solution of the product of Example 15 (2.0 g, 5.2 mmol) in methanol (300 ml) was stirred with 10% pd/c (20 mg) under hydrogen at room temperature for 4 hr. The catalyst was filtered off, and the filtrate was evaporated to yield a solid, which was purified by column chromatography [Silica gel (100 g) with dichloromethane:acetone:methanol=100:10:5 as an eluant] to give 16 (1.6 g): Yield 80%; mp 220°-224° C.; crystals from methanol; $[\alpha]_D^{25}$ −116° C. (c=0.25 acetone); ¹H NMR (d₆-acetone) δ 7.40 (d, 1H, 3′-OH), 7.32 (s, 1H, 4′-OH), 6.94 (s, 1H, 5-H), 6.52 (5, 1H, 6′-H), 6.47 (s, 1H, 8H), 5.99 (s, 2H, OCH₂O), 5.95 (s, 1H, 2′-H), 5.62 (s 1H, 4-OH), 4.89 (d, J=3.1 Hz, 1H, 4-H), 4.52 (d, J=4.9 Hz, 1H, 1-H), 4.32 (m, 2H, 11-H), 3.73 (s, 3H, 5′-OCH₃), 5.28 (dd, J=14.1, 4.9 Hz, 1H, 2-H), 2.94 (m, 1H, 3-H); IR (KBr) 3460, 2900, 1740, 1605 and 1470 cm⁻¹.

General procedure for the synthesis of Examples 17 to 23.

A suspension containing 3′,4′-O-didemethylepipodophyllotoxin (1.0 g, 2.4 mmol) in dry dichloromethane (35 ml) was kept at 0° C., and then bubbled with dry hydrogen bromide for 30 min. After removing the ice-water bath, the reaction was continued for 1 hr. the mixture was azeotropically distilled in vacuo with benzene to remove the water resulting from the reaction. The crude bromide (1.2 g) was used for next step.

A solution of the aforementioned bromide (500 mg, 1.11 mmol), anhydrous barium carbonate (439 mg, 2.33 mmol), and the appropriate substituted aniline (1.16 mmol) in 8 ml of freshly distilled THF under nitrogen was stirred overnight at room temperature. The mixture was filtered and the filtrate was evaporated to yield a solid. The solid was purified by preparative TLC (Silica gel, toluene:ethylacetate:methanol=9:3:0.2) to afford the desired products (Examples 17 to 23). The yields of these compounds from the starting material were in a range of 15-35%.

EXAMPLE 17

3′,4′-O-Didemethyl-4β-anilino-4-desoxypodophyllotoxin mp 170°-173° C.; crystals from ether; $[\alpha]_D$ −60° (c=0.1, acetone); ¹H NMR (CDCl₃) δ 7.20 (t, J=7.8 Hz, 2H, 3″,5″-H), 6.76 (t, J=7.8 Hz, 1H, 4″-H), 6.74 (d, J=1.8 HZ, 1H, 6′-H), 6.73 (s, 1H, 5-H), 6.51 (d, J=7.8 Hz, 2H, 2″,6″-H), 6.48 (s, 1H, 8-H), 5.92 and 5.93 (s each, 2H, OCH₂O), 5.84 (d, J=1.8 Hz, 1H,2′-H), 4.64 (dd, J=5.4, 4.4 Hz, 1H, 4-H), 4.54 (d, J=4.8 Hz, 1H,1-H), 4.35 (dd, J=8.4, 7.3 Hz, 1H, 11-H), 3.97 (dd, J=10.2, 8.4 Hz, 1H, 11-H), 3.87 (s, 3H, OCH₃), 3.79 (d, J=6.0 Hz, 1H, exchangeable, NH), 3.12 (dd, J=13.9, 4.6 Hz, 1H, 2-H), 3.04 (m, 1H, 3-H); IR (KBr) 3450, 3400, 1770, 1600, 1500 and 1480 cm⁻¹.

EXAMPLE 18

3′,4′-O-didemethyl-4β-(4″-floroanilino)-4-desoxypodophyllotoxin mp 175°-178° C.; crystals from ether; $[\alpha]_D^{25}$ −123° (c=0.3, acetone); ¹NMR (CDCl₃) δ 6.91 (dd, J=8.9, 8.6 Hz, 2H, 3″,5″-H), 6.73 (d, J=1.5 Hz, 1H, 6′-H), 6.70 (s, 1H, 5-H), 6.44 (d, J=8.9, 4.1 Hz, 2H, 2″,6″-H), 6.47 (s, 1H, 8-H), 5.92 and 5.93 (s each, 2H, OCH₂O), 5.83 (d, J=1.5 Hz, 1H, 2′-H), 5.32-5.27(brs, 2H, 4′,5′-OH) 4.54 (d, J=4.0 Hz, 1H, 4-H), 4.52 (d, J=4.7, 1H, 1-H), 4.33 (dd, J=8.2, 7.6 Hz, 1H, 11-H), 3.86 (s, 3H, 3′-OCH₃), 3.95 (dd, J=9.7, 8.2 Hz, 1H, 11-H), 3.70 (brs, 1H, NH) 3.10 (dd, J=14.0, 4.9 Hz, 1H, 2-H), 3.02 (m, 1H, 3-H); IR (KBr) 3450, 3400, 1765, 1610, 1500 and 1475 cm⁻¹.

EXAMPLE 19

3′,4′-O-Didemethyl-4β-(3″-hydroxyanilino)-4-desoxypodophyllotoxin mp 218°-220° C., crystals from ether; $[\alpha]_D^{25}$ −64° (c=0.07, acetone); ¹H NMR (CDCl₃) δ 7.03 (t, J=8.0 Hz, 1H, 5″-H), 6.72 (d, overlap, 1H, 6′-H), 6.72 (s, 1H, 5-H), 6.48 (s, 1H, 8-H), 6.22 (dd, J=8.1, 2.0 Hz, 1H, 6″-H), 6.10 (dd, J=8.1, 2.0 Hz, 1H, 4″-H), 6.02 (dd, J=2.0, 1.5 Hz, 1H, 2″-H), 5.93 (brs, 2H, OCH₂O), 5.84 (d, J=1.6 Hz, 1H, 2′-H), 5.31 (brs, 1H, 4′-OH), 5.23 (brs, 1H, 5'-OH), 4.61 (t, J=5.5 Hz, 1H, 4-H), 4.53 (d, J=4.7 Hz, 1H,1-H), 4.35 (dd, J=8.4, 7.6 Hz, 1H, 11-H), 3.98 (dd, J=10.1, 8.4 Hz, 1H, 11-H), 3.87 (s, 3H, 3'-OCH$_3$), 3.80(d, J=5.5 Hz, 1H, NH), 3.10 (dd, J=13.9, 4.7 Hz, 1H, 2-H), 3.02 (m, overlap, 1H, 3-H).

EXAMPLE 20

3',4'-O-Didemethyl-4β-(3",4"-methylenedioxyanilino)-4-desoxypodophyllotoxin mp 181°-183° C.; crystals from ether; [α]$_D^{25}$ −69° (c=0.2, acetone); $^1$H NMR (CDCl$_3$) δ 6.73 (d, J=8.6 Hz, 1H, 5"-H), 6.71 (s, 1H, 5-H), 6.70 (d, J=1.7 Hz, 1H, 6'-H), 6.47 (s, 1H, 8-H), 6.05 (d, J=2.7 Hz, 1H, 2"-H), 6.03 (dd, J=8.6, 2.7 Hz, 1H, 6"-H), 5.92 and 5.93 (s each 2H, OCH$_2$O), 5.85 (d, J=1.7 Hz, 1H, 2'-H), 5.36 (brs, 1H, OH), 4.53 (d, J=3.7 Hz, 1H, 4-H), 4.51 (d, J=4.8, 1H,1-H), 4.35 (dd, J=8.3, 7.5 Hz, 1H, 11-H), 4.00(dd, J=10.4, 8.3 Hz, 1H, 11-H), 3.86 (s, 3H, 3'-OCH$_3$), 4.22(m, 4H, 3",4"-OCH$_2$CH$_2$O—), 3.65 (brs, 1H, NH), 3.12 (dd, J=14, 5.0 Hz, 1H, 2-H), 3.00 (m, 1H, 3-H); IR (KBr) 3450, 3400, 1760, 1605, 1505 and 1475 cm$^{-1}$.

EXAMPLE 21

3',4'-O-Didemethyl-4β-(3"-methoxycarbonylanilino)-4-desoxypodophyllotoxin mp 167°-170° C.; crystals from ether; [α]$_D^{25}$ −84° (c=0.4 acetone); $^1$H NMR (CDCl$_3$) δ 7.44 (d, J=7.6 Hz, 1H, 4"-H), 7.24 (t, J=7.6 Hz, 1H, 5"-H), 7.18 (brs, 1H, 2"-H), 6.7 (m, overlap, 1H, 6"-H), 6.73 (d, J=1.8 Hz, 1H, 6'-H), 6.71 (s, 1H, 5-H), 6.49 (s, 1H, 8-H), 5.93 and 5.94 (s each, 2H, OCH$_2$O), 5.84 (d, J=1.7 Hz, 1H, 2'-H), 5.27 (brs, 1H, 4'-OH), 5.16 (brs, 1H, 5'-OH), 4.76 (dd, J=5.7, 3.5 Hz 1H, 4-H), 4.54 (d, J=4.0 Hz, 1H, 1-H), 4.38 (dd, J=6.8, 6.2 Hz, 1H, 11-H), 3.90 (dd, overlap 1H, 11-H), 3.89 (s, 3H, 3"-COOCH$_3$) 3.87 (s, 3H, 3'-OCH$_3$), 3.09 (brs, overlap, 2H, 2, 3-H); IR (KBr) 3450, 3390, 1770, 1600, 1510 and 1480 cm$^{-1}$.

EXAMPLE 22

3',4'-O-Didemethyl-4β-(4"-cyanoanilino)-4-desoxypodophyllotoxin mp 210°-212° C., crystals from ether; [α]$_D^{25}$ −114° (c=0.1, acetone); $^1$H NMR (CDCl$_3$) δ 7.48 (d, J=8.7 Hz, 2H, 3",5"-H), 6.74 (d, J=1.6 Hz, 1H, 6'-H), 6.69 (s, 1H, 5-H), 6.53 (d, J=8.7 Hz, 2H, 2",6"-H), 6.50 (s, 1H, 8-H), 5.95 (s, 2H, OCH$_2$O), 5.80 (d, J=1.6 Hz, 1H, 2'-H), 5.29 (s, 1H, 4'-OH), 5.24 (s, 1H, 5'-OH), 4.71 (m, 1H, NH), 4.55 (d, J=4.0 Hz, 1H, 1-H), 4.31 (dd, overlap, 1H, 11-H), 4.30 (d, overlap, 1H, 4-H), 3.87 (s, 3H, —OCH$_3$), 3.86 (dd, J=10.9, 8.7 Hz, 1H, 11-H), 3.06 (dd, J=14.0, 4.3 Hz, 1H, 2-H), 3.06 (m, overlap, 1H, 3-H); IR (KBr) 3450, 3360, 2200, 1765, 1600, 1510 and 1475 cm$^{-1}$.

EXAMPLE 23

3',4'-O-Didemethyl-4β-(4"-nitroanilino)-4-desoxypodophyllotoxin mp 208°-210° C.; crystals from ether; [α]$_D^{25}$ −105° (c=0.1 acetone) $^1$H NMR (CDCl$_3$) δ 8.13 (d, J=8.9 Hz, 2H, 3",5"-H), 6.73 (d, J=1.8 HZ, 1H, 6'-H), 6.70 (s, 1H, 5-H), 6.53 (d, J=8.9 Hz, 2H, 2",6"-H), 6.51 (s, 1H, 8-H), 5.94 (s, 2H, OCH$_2$O), 5.80 (d, J=1.8 Hz, 1H, 2'-H), 5.32 (s, 1H, 4'-OH), 5.21 (s, 1H, 5'-OH), 4.79 (m, 1H, NH), 4.56 (d, J=4.7 Hz, 1H, 1-H), 4.56 (d, overlap, 1H, 4-H), 4.36 (dd, J=9.0, 7.1 Hz, 1H, 11-H), 3.87 (s, 3H, 3'-OCH$_3$), 3.85 (dd, J=11.2, 9.0 Hz, 1H, 11-H), 3.08 (m, overlap, 1H, 3-H), 3.02 (dd, J=14.3, 4.8 Hz, 1H, 2-H); IR (KBr) 3450, 3380, 1760, 1590, 1490 and 1470 cm$^{-1}$.

EXAMPLES 24 and 25

6,7-O-Demethylenepodophyllotoxin (24) and 6,7-O-demethylene-4'-O-demethylpodophyllotoxin (25)

To a dichloromethane (200 ml) solution containing boron trichloride (0.12 mole) at −70°--65° C. was added dropwise podophyllotoxin (12.4 g, 30 mmol) in CH$_2$Cl$_2$ (for 2 hr. The reaction was continued at the same temperature for an additional 1 hr. The mixture was poured into 500 ml of ice-water, extracted with ethyl acetate. The combined organic layers were washed with brine until pH=5-6, dried (Na$_2$SO$_4$), and filtered. The filtrate was evaporated to give a white solid (12.7 g). The solid was refluxed with a mixture of acetone-water-calcium carbonate (12 ml-120 ml-8 g) for 3.5 h. The white suspension was filtered off, and the filtrate was neutralized by 1N hydrochloric acid to pH=2-3, and then extracted with ethyl acetate. The combined organic layers were washed with brine, dried (Na$_2$SO$_4$), and evaporated to afford a mixture of 29 and 30, which was purified by flash column chromatography [silica gel (200 g), chloroform-acetone-methanol (100-10-5)] to give 9.3 g of 24: mp 226°-228° C.; crystals from ethyl acetate; [α]$_D^{25}$ −120° (c=0.5, C$_2$H$_5$OH); $^1$H NMR (d$_6$-acetone) δ 7.9 (brs, 2H, 6,7-OH), 7.20 (s, 1H, 5-H), 6.47 (s, 1H, 8H), 6.46 (s, 2H, 2',6'-H), 4.75 (d, J=9.7 Hz, 1H, 4-H), 4.50 (t, 2H, 11-H, and 1-H), 4.12 (t, J=10.3 Hz, 1H, 11-H), 3.68 (s, 9H, 3'4',5'-OCH$_3$), 3.04 (dd, J=14.3, 4.8 Hz, 1H, 2-H), 2.83 (m, 1H, 3-H); IR (KBr) 3518, 3400, 3000, 1760, 1578 and 1500 cm$^{-1}$.

Compound 25 was obtained from the aforementioned flash column by further elution as a white solid (0.9 g): crystals from ethyl acetate; mp 208°-211° C. (dec); [α]$_D^{25}$ −101° (c=0.25. Acetone); $^1$H NMR (d$_6$-Acetone) δ 7.88 and 7.84 (s each, 2H, 6,7-OH), 7.19 (s, 1H, 5-H), 7.07 (s, 1H, 4'-OH). 6.47 (s, 1H, 8-H), 6.45 (s, 2H, 2',6'-H), 4.74 (d, J=9.5 Hz, 1H, 4-H), 4.71 (s, 1H, 4'-OH), 4.49 (m, 2H, 11-H and 1-H), 4.11 (t, J=10.2 Hz, 1H, 11-H), 3.69 (s, 6H, 3',5'-OCH$_3$), 2.96 (dd, J=14.2, 4.9 Hz, 1H, 2-H), 2.87 (m, 1H, 3-H); IR (KBr) 3430, 3160, 1772, 1638 and 1540 cm$^{-1}$.

GENERAL PROCEDURE FOR THE SYNTHESIS OF EXAMPLES 26-30

Through a suspension of compound 25 (5.5 g, 11.8 mmol) in dry dichloromethane (150 ml) cooled at 0°-5° C. was bubbled hydrogen bromide for 1h. The solution was azeotropically distilled with benzene to remove the water. The crude product (6.4 g) was used for the preparation of Examples 26-31.

A solution containing 25 (30 mg, 0.66 mmol), anhydrous barium carbonate (260 mg, 1.32 mmol), and the appropriate substituted aniline (0.66 mmol) in dry THF (5 ml) was stirred under nitrogen for 2-3 h at room temperature. The barium salts were filtered, and the filtrate was evaporated to dryness. The solid was purified via flash column chromatography [silica gel (10 g), TLC standard grade, toluene:ethylacetate (25:40)]. The yields were in a range of 40-80%.

EXAMPLE 26

6,7-O-Demethylene-4'-O-demethyl-4β-anilino-4-desoxypophyllotoxin mp 150°-153° C.; crystals from ethyl acetate; [α]$_D^{25}$ −112° (c=0.2, acetone); $^1$H NMR (d$_6$-acetone) δ

8.02 (brs, 2H, 6,7-OH), 7.13 (t, 3H, 4'-OH and 3'',5''-H), 6.78 (s, 1H, 5-H), 6.72 (d, J=8.0 Hz, 1H, 4''-H), 6.62 (t, J=7.7 Hz, 2H, 2'',6''-H), 6.38 (s, 1H, 2',6'-OCH$_3$), 5.19 (d, 1H, NH), 4.82 (d, J=3.9 Hz, 1H, 4-H), 4.46 (d, J=4.9 Hz, 1H, 1-H), 4.40 (t, 1H, 11-H), 3.89 (t, 1H, 11-H), 3.68 (s, 6H, 3'',5''-OCH$_3$), 3.25 (dd, J=14.0, 4.9 Hz, 1H, 2-H), 3.12 (m, 1H, 3-H): IR (KBr) 3400, 3180, 1760, 1605 and 1515 cm$^{-1}$.

EXAMPLE 27

6,7-O-Demethylene-4'-O-demethyl-4β-(4''-nitroanilino)-4-desoxypodophyllotoxin mp 185°–188° C. (dec); [α]$_D^{25}$ –130° (c=0.25, acetone); $^1$H NMR (D$_6$-acetone) δ 8.04 (d, J=8.9 Hz, 2H, 3'',5''-H), 6.89 (d, J=8.9 Hz, 2H, 2'',6''-H), 6.82 (s, 1H, 5-H), 6.68 and 6.65 (s and s, 2H; 6,7-OH), 6.52 (s, 1H, 8-H), 6.37 (s, 2H, 2',6'-H), 5.13 (brs, 1H, 4-H), 4.51 (d, 1H, 1-H), 4.43 (t, 1H, 11-H), 3.85 (t, 1H, 11-H), 3.68 (s, 6H, 3',5'-OCH$_3$), 3.22 (m, 2H, 2-H and 3-H); IR (KRr) 3370, 2940, 1765, 1600, 1518 and 1320 cm$^{-1}$.

EXAMPLE 28

6,7-O-Demethylene-4'-O-demethyl-4β-[4''-(ethoxycarbonyl)anilino]-4-desoxypodophyllotoxin mp 147°–152° C.; crystals from dichloromethane-ethyl acetate; [α]$_D^{25}$ 104° (c=0.5, acetone); $^1$H NMR (d$_6$-acetone) δ 7.99 and 7.96 (s and s, 2H, 6,7-OH), 7.83 (d, J=8.8 Hz, 2H, 3'',5''-H), 7.09 (s, 1H, 4'-OH), 6.81(d, J=8.8 HZ, 2H, 2'',6''-H), 6.79 (s, 1H, 5-H), 6.52 (s, 1H, 8-H), 6.40 (s, 2H, 2',6'-H), 6.02 (d, 1H, NH), 5.02 (dd, J=6.9, 2.7 Hz, 1H, 4-H), 4.50 (d, J=4.3 Hz, 1H, 1-H), 4.41 (t, J=6.7 Hz, 1H, 11-H), 3.85 (t=6.7 Hz, 1H, 11-H), 3.69 (s, 6H, 3',5'-OCH$_3$), 3.28–3.10 (m, 2H, 2-H and 3-H); IR (KBr) 3360, 2950, 1750, 1675, 1595 and 1510 cm$^{-1}$; Anal. for C$_{29}$H$_{29}$NO$_9$; C, 65.04; H, 5.46; N. 2.61; Found C, 64:82; H, 5.82, N, 2.61.

EXAMPLE 29

6,7-O-Demethylene-4'-O-demethyl-4β-(cyanoanilino)-4-deoxypodophyllotoxin mp 153°–156° C. (dec); crystals from ethylacetate-toluene; [α]$_D^{25}$ –108° (c=0.5, acetone); $^1$H NMR (d$_6$-acetone) δ 8.08 and 8.00 (s and s, 2H, 6,7-OH), 7.50 (d, J=8.7 Hz, 2H, 3'',5''-H), 7.13 (s, 1H, 4'-OH), 6.89(d, J=8.7 Hz, 2H, 2'',6''-H), 6.81 (s, 1H, 5-H), 6.53 (s, 1H, 8-H), 6.38 (s, 2H, 2',6'-H), 6.21(d, J=8.6 Hz, 1H, NH), 5.03 (dd, 1H, 4-H), 4.51 (d, J=4.2 Hz, 1H, 1-H), 4.42(t, 1H, 11-H), 3.84 (dd, 1H, 11-H), 3.68(s, 6H, 3',5'-OCH$_3$), 3.20(m, 2H, 2-H and 3-H); IR (KBr) 3360, 2920, 2200, 1755, 1596 and 1510 cm$^{-1}$.

EXAMPLE 30

6,7-O-Demethylene-4'-O-demethyl-4β-(fluoroanilino)-4-desoxypodophyllotoxin mp 151°–153° C.; crystals from ethyl acetate-toluene; [α]$_D^{25}$ –80° (c=0.5 acetone); $^1$H NMR (d$_6$-acetone) δ 7.97 and 7.96 (s and s, 2H, 6,7-OH), 7.04(s, 1H, 4'-OH), 6.94(t, 2H, 3'',5''-H), 6.86 (m, 3H, 5H and 2'',6''-H), 6.51 (s, 1H, 8-H), 6.40 (s, 2H, 2',6'-H), 5.18 (d, 1H, NH), 4.80(d, J=4.1 HZ, 1H, 4-H), 4.51 (d, J=4.9 Hz, 1H, 1-H), 4.41(t, 1H, 11-H), 3.91 (t, 1H, 11-H), 3.69 (s, 6H, 3',5'-OCH$_3$), 3.26 (dd, J=13.1, 7.7 Hz, 1H, 2-H), 3.09 (m, 1H, 3-H); IR (KBr) 3400, 2950, 1755, 1615 and 1510 cm$^{-1}$.

Examples 31–33 were prepared according to the method analogous to that of examples 26–30. The yields were in the range of 25–40%.

EXAMPLE 31

6,7-O-demethylene-6,7-O-dimethyl-4'-O-demethyl-4β-(4''-fluoroanilino)-4-desoxypodophyllotoxin mp 221°–224° C.; $^1$H NMR (CDCl$_3$) δ 6.96 (t, 2H, 3''-H and 5''-H), 6.74 (s, 1H, 5-H), 6.55 (s, 1H, 8-H), 6.50 (t, 2H, 2''-H and 6''-H), 6.34 (s, 2H, 2'-H and 6'-H), 5.43 (s, 1H, 4'-OH), 4.65 (m, 2H, 1-H and 4-H), 4.39 (t, 1H, 11-H), 4.00 (t, 1H, 11-H), 3.86 (s, 3H, 6-OCH$_3$), 3.82 (s, 3H, 7-OCH$_3$), 3.75 (s, 6H, 3', 5'-OCH$_3$), 3.18 (dd, J=14.7, 4.9 Hz, 1H, 2-H), 3.01 (m, 1H, 3-H); IR (KBr) 3380, 2940, 1760, 1660, 1510 and 1460 cm$^{-1}$; Anal. Calcd for C$_{28}$H$_{28}$FNO$_7$·½H$_2$O: C. 65.42, H. 5.59, N. 2.27. Found C. 65.44, H. 5.75, N. 2.66.

EXAMPLE 32

6,7-O-demethylene-6,7-O-dimethyl-4'-O-demethyl-4β-(4''-cyanoanilino)-4-desoxypodophyllotoxin mp 158°–161° C.; $^1$H NMR (CDCl$_3$) δ 7.52 (d, J=8.0 Hz, 2H, 3''-H and 5''-H), 6.73 (s, 1H, 5-H), 6.60 (d, J=8.0 Hz, 2H, 2''-H and 6''-H), 6.57 (s, 1H, 8-H), 6.32 (s, 2H, 2'-H and 6'-H), 5.44 (s, 1H, 4'-OH), 4.81 (t, 1H, 4-H), 4.68 (d, J=3.6 Hz, 1H, 1-H), 4.40 (s.brs, 2H, 11-H), 3.88 (s, 3H, 6-OCH$_3$), 3.81 (s, 3H, 7-OCH$_3$), 3.79 (s, 6H, 3', 5'-OCH$_3$), 3.01 (m, 2H, 2-H and 3-H); IR (KBr) 3360, 2920, 2210, 1770, 1600, 1520 and 1460 cm$^{-1}$; Anal. Calcd for C$_{29}$H$_{28}$N$_2$O$_7$·½C$_6$H$_5$CH$_3$: C.69.38, H. 5.73, N. 4.98. Found C. 69.26, H. 5.90, N. 4.79.

EXAMPLE 33

6,7-O-demethylene-6,7-O-dimethyl-4'-O-demethyl-4β-[4''-(ethoxycarbonyl)anilino]-4-desoxypodophyllotoxin mp 125°–127° C.; $^1$H NMR (CDCl$_3$) δ 7.95 (d, J=8.7 Hz, 2H, 3''-H and 5''-H), 6.76 (s, 1H, 5-H), 6.58 (d, J=8.7 Hz, 2H, 2''-H and 6''-H), 6.56 (s, 1H, 8-H), 6.33 (s, 2H, 2''-H and 6''H), 5.44 (s, 1H, 4'-OH), 4.82 (t, 1H, 4-H), 4.67 (d, J=4.5 Hz, 1H, 1-H), 4.36 (t, J=7.3 Hz, 1H, 11-H), 4.33 (q, J=7.0 Hz, 2H, CO$_2$CH$_2$CH$_3$), 3.94 (t, 1H, 11-H), 3.87 (s, 3H, 6-OCH$_3$), 3.82 (s, 3H, 7-OCH$_3$), 3.79 (s, 6H, 3', 5'-OCH$_3$), 3.14 (dd, J=13.3, 4.5 Hz, 1H, 2-H), 3.05 (m, 1H, 3-H), 1.38 (t, J=7.0 Hz, 3H, CO$_2$CH$_2$CH$_3$); IR (KBr) 3360, 2940, 1770, 1680, 1600, 1510 and 1460 cm$^{-1}$; Anal. Calcd for C$_{31}$H$_{33}$NO$_9$: 66.06, H. 5.90, N. 2.49. Found C. 66.23, H. 6.32, N. 2.30.

GENERAL PROCEDURE OF THE SYNTHESIS OF EXAMPLES 34–42

To a solution of appropriately substituted benzoic acid (0.25 mmol) in THF (3 ml) was added DCC (57 mg, 0.28 mmol). After 10 min, compound 2 (100 mg, 0.25 mmol) was added. After the reaction mixture was stirred overnight, it was filtered, and the filtrate was evaporated in vacuo. The crude product was purified by preparative TLC [chloroform:ethyl acetate:acetone:methanol (100:5:5:5)] to give the desired product.

EXAMPLE 34

4'-O-Demethyl-4β-(benzoylamino)-4-desoxypodophyllotoxin

Yield 73%; mp 213°–214° C.; crystals from chloroform-ethyl acetate; $^1$H NMR (CDCl$_3$) δ 7.78 (d, J=7.4 Hz, 2H, 2'',6''-H), 7.57–7.45 (m, 3H, 3'',4'',5''-H), 6.83 (s, 1H, 5-H), 6.57 (s, 1H, 8-H), 6.33 (s, 2H, 2',6'-H), 6.27 (d, J=6.8 Hz, 1H, 4-H), 6.01 and 5.99 (s and s, 2H, OCH₂O), 5.45 (brs, 2H, NH and 4'-OH), 4.64 (d, 1H, J=4.3 Hz, 1H, 1-H), 4.51 (t, J=9.2 Hz, 1H, 11-H), 3.92 (t, J=9.2 Hz, 1H, 11-H), 3.80 (s, 6H, 3',5'-OCH₃), 3.06 (m, 1H, 3-H), 2.93 (dd, J=14.2, 4.8 Hz, 1H, 2-H); IR (KBr) 3500, 3300, 2910, 1750, 1720, 1610, 1500 and 1470 cm⁻¹.

EXAMPLE 35

4'-O-Demethyl-4β-[(2-hydroxylbenzoyl)amino]-4-desoxypodophyllotoxin

Yield 61%; mp 172°–174° C.; crystals from chloroform-ethyl acetate; ¹H NMR (CDCl₃) δ 7.45 (t, J=7.5 Hz, 1H, 4''-H), 7.35 (d, J=7.5 Hz, 1H, 6''-H), 7.04 (d, J=7.5 Hz, 1H, 3''-H), 6.88 (t, J=7.6 Hz, 1H, 5''-H), 6.82 (s, 1H, 5-H), 6.58 (s, 1H, 8-H), 6.47 (d, J=6.7 Hz, 1H, 4-H), 6.40 (s, 2H, 2',6'-H), 6.01 and 6.00 (s and s, 2H, OCH₂O), 5.44 (brs, 2H, NH and 4'-OH), 4.64 (d, J=4.9 Hz, 1H, 1-H), 4.49 (t, 1H, 11-H), 3.87 (m, 1H, 11-H), 3.76 (6H, s, 3',5'-OCH₃), 3.05 (m, 1H, 3-H), 2.96 (dd, J=14.3, 4.9 Hz, 1H, 2-H); IR (KBr) 3490, 3350, 3120, 2905 1760, 1630, 1590, 1550 and 1470 cm⁻¹.

EXAMPLE 36

4'-O-Demethyl-4β-[(4''-fluorobenzoyl)amino]-4-desoxypodophyllotoxin

Yield 69%; mp 242°–244° C.; crystals from chloroform-ethyl acetate; ¹H NMR (CDCl₃) δ δ 7.80 (m, 2H, 2'',6''-H), 7.16 (m, 2H, 3'',5''-H), 6.82 (s, 1H, 5-H), 6.57 (s, 1H, 8-H), 6.33 (s, 2H, 2',6'-H), 6.25 (d, J=6.8 Hz, 1H, 4-H), 6.01 and 6.00 (s and s, 2H, OCH₂O), 5.43 (brs, 2H, NH and 4'-OH), 4.63 (d, J=4.7 Hz, 1H, 1-H), 4.50 (t, 1H, 11-H), 3.87 (m, 1H, 11-H), 3.80 (s, 6H, 3',5'-OCH₃), 3.04 (m, 1H, 3-H), 2.93 (dd, J=14.2, 4.7 Hz, 1H, 2-H); IR (KBr) 3410, 3120, 2910, 1760, 1630, 1590, 1510 and 1480 cm⁻¹; Anal. Calcd. for C₂₈H₂₄NFO₈ C. 64.49; H. 4.61; N. 2.69. Found C. 64.31; H.5.09; N. 2.61.

EXAMPLE 37

4'-O-Demethyl-4β-[(4-acetoxybenoyl)amino]-4-desoxypodophyllotoxin

Yield 51%; mp 175°–176° C.; crystals from hexane-ethyl acetate; ¹H NMR (CDCl₃) δ 8.12 (d, J=8.7 Hz, 2H, 2'',6''-H), 7.19(d, J=8.7 Hz, 2H, 3'',5''-H), 6.82(S, 1H,5-H), 6.57 (s, 1H, 8-H), 6.33 (s, 2H, 2',6'-H), 6.25(d, J=6.8 Hz, 1H, 4-H), 6.01 and 6.00 (s and s, 2H, OCH₂O), 5.43 (brs, 2H, NH and 4'-OH), 4.63 (d, J=4.7 Hz, 1H, 1-H), 4.50 (m, 1H, 11-H), 3.86 (m, 1H, 11-H), 3.76 (s, 6H, 3',5'-OCH₃), 3.04 (m, 1H, 3-H), 2.96 (dd, J=14.3, 4.8 Hz, 1H, 2-H), 2.33 (s, 3H, CH₃CO₂), IR (KBr) 3350, 3100, 2980, 1760, 1740, 1620, 1590, 1505 and 1470 cm⁻¹; Anal. Calcd for C₃₀H₂₇NO₁₀; C. 64.17; H. 4.81; N. 2.50. Found C. 64.01; H. 4.99; N. 2.44.

EXAMPLE 38

4'-O-Demethyl-4β-[(4''-acetylbenzoyl)]amino]-4-desoxypodophyllotoxin

Yield 70%; mp 178°–180° C. (dec), crystals from hexane-ethyl acetate; ¹H NMR (CDCl₃) δ 8.05 (d, J=8.2 Hz, 2H, 3'',5''-H), 7.87 (d, J=8.2 Hz, 2H, 2'',6''-H), 6.83 (s, 1H, 5-H), 6.58 (s, 1H, 8-H), 6.36 (m, 3H, 2',6'-H and 4-H), 6.02 and 6.00 (s and s, 2H, OCH₂O), 5.45 (brs, 2H, NH and 4'-OH), 4.64 (d, J=4.8 Hz, 1H, 1-H), 4.51 (t, 1H, 11-H), 3.89 (m, 1H, 11-H), 3.73 (s, 6H, 3',5'-OCH₃), 3.06 (m, 1H, 3-H), 2.94 (dd, J=14.2, 4.8 Hz, 1H, 2-H), 2.66 (s, 3H, CH₃CO); IR (KBr) 3500, 3350, 2920, 1770, 1680, 1640, 1600, 1520 and 1480 cm⁻¹.

EXAMPLE 39

4'-O-Demethyl-4β-[(3''-cyanobenzoyl)amino]-4-desoxypodophyllotoxin

Yield 68%; mp 190°–192° C., crystals from hexane-ethyl acetate; ¹H NMR (CDCl₃) δ 8.06 (m, 2H, 2',6'-H), 7.84 (d, J=7.5 Hz, 1H, 4''-H), 7.62 (t, J=7.5 Hz, 1H, 5''-H), 6.82 (s, 1H, 5-H), 6.58 (s, 1H, 8-H), 6.38 (d, J=6.7 Hz, 1H, 4-H), 6.33 (s, 2H, 2',6'-H), 6.02 and 6.00 (s and s, 2H, OCH₂O), 5.45 (brs, 2H, NH and 4'-OH), 4.64 (d, J=4.8 Hz, 1H, 1-H), 4.50 (t, 1H, 11-H), 3.87 (t, 1H, 11-H), 3.80 (s, 6H, 3',5'-OCH₃), 3.07 (m, 1H, 3-H), 2.94 (dd, 1H, J=14.3, 4.9 Hz, 2-H), IR (KBr) 3300, 3100, 2910, 2200, 1760, 1640, 1590, 1500 and 1470 cm⁻¹.

EXAMPLE 40

4'-O-Demethyl-4β-[(4''-cyanobenzoyl)amino]-4-desoxypodophyllotoxin

Yield 73%; mp 198°–202° C., crystals from chloroform-ethyl acetate; ¹H NMR (CDCl₃) δ 7.89 (d, J=8.5 Hz, 2H, 3'',5''-H), 7.77 (d, J=8.5 Hz, 2H, 2'',6''-H), 6.81 (s, 1H, 5-H), 6.58 (s, 1H, 8-H), 6.33 (m, 3H, 2'',6''-H and 4-H), 6.02 and 6.00 (s and s, 1H, OCH₂O), 5.44 (brs, NH and 4'-OH), 4.64 (d, J=5.0 Hz, 1H, 1-H), 4.50 (t, 1H, 11-H), 3.83 (t, 1H, 11-H), 3.80 (s, 6H, 3',5'-OCH₃), 3.06 (m, 1H, 3-H), 2.91 (dd, J=14.3, 5.0 Hz, 1H, 2-H), IR (KBr) 3320, 3100, 2980, 2200, 1760, 1640, 1600, 1500 and 1470 cm⁻¹.

EXAMPLE 41

4'-O-Demethyl-4β-[(3''-nitrobenzoyl)amino]-4-desoxypodophyllotoxin

Yield 80%; mp 194°–195° C., crystals from chloroform-ethyl acetate; ¹H NMR (CDCl₃) δ 8.58 (s, 1H, 2''-H), 8.38 (d, J=7.5 Hz, 1H, 4''-H), 8.21 (d, J=7.5 Hz, 1H, 6''-H), 7.26 (t, 5''-H), 6.82 (s, 1H, 5-H), 6.54 (m, 2H, 4-H and 8-H), 6.32 (s, 2H, 2',6'-H), 6.00 (s, 2H OCH₂O), 5.45 (brs, 2H, NH and 4'-OH), 4.62 (d, J=4.7 Hz, 1H, 1-H), 4.49 (t, 1H, 11-H), 3.87 (t, 1H, 11-H), 3.80 (s, 6H, 3',5'-OCH₃), 3.08 (m, 1H, 3-H), 2.96 (dd, J=14.4, 4.8 Hz, 1H, 2-H), IR (KBr) 3320, 3100, 2980, 2200, 1760, 1640, 1600, 1500 and 1470 cm⁻¹.

EXAMPLE 42

4'-O-Demethyl-4β-[(3''-aminobenzoyl)amino]-4-desoxypodophyllotoxin

A solution of the product from Example 41 (25 mg. 0.05 mmol) in ethyl acetate (3.0 ml) was stirred under hydrogen in the presence of 10% Pd/C (3 mg) at room temperature for 2 hr. The catalyst was removed by filtration, and the filtrate was evaporated to afford the desired product (20 mg): Yield 95%; mp 180°–182° C., crystals from chloroform-ethyl acetate; ¹H NMR δ 7.20 (t, J=7.6 Hz, 1H, 5''-H), 7.11 (s, 1H, 2''-H), 7.02 (d, J=7.6 Hz, 1H, 6''-H), 6.82 (m, 2H, 4''-H and 5-H), 6.55 (s, 1H, 8-H) 6.32 (s, 2H, 2',6'-H), 5.98 (d, J=5.1 Hz, 1H, 4-H), 5.99 and 5.97 (s and s, 2H, OCH₂O), 5.40 (brs, 2H, NH and 4'-OH), 4.61 (d, J=4.6 Hz, 1H, 1-H), 4.48 (t, 1H, 11-H), 3.85 (m, 1H, 11-H), 3.79 (s, 6H, 3',5'-OCH₃), 3.01 (m, 1H, 3-H), 2.90 (dd, J=14.3, 4.9 Hz, 1H, 2-H), IR (KBr) 3360, 3120, 2920, 1760, 1640, 1600, 1570 and 1460 cm⁻¹; Anal. Calcd for C₂₈H₂₆N₂O₈; C,64.86; H, 5.02; N. 5.41. Found C,64.73; H, 5.24; N, 5.25.

GENERAL PROCEDURE FOR THE SYNTHESIS OF EXAMPLES 43 TO 45

To a solution of the compounds from examples 18, 21 and 23 (0.1 mmol) in ether (0.5 ml) was added tetrachloro-1,2-benzoquinone (0.15 mmol) in ether (0.5 ml) at room temperature. After stirring for 10 min., the reaction mixture was filtered, and the solid was collected, washed with ether, and dried to give the compounds described in examples 43 to 45 with a range of yields of 90 to 100%.

EXAMPLE 43

3',4'-Didemethoxy-3',4'-dioxo-4β-(4''-fluoroanilino)-4-desoxypodophyllotoxin mp 193°–194° C. (dec), crystals from ether; $^1$H NMR (CDCl$_3$) δ 6.93 (dd, J=8.6, 8.4 Hz, 2H, 3'',5''-H), 6.69 (s, 1H, 5-H), 6.51 (s, 1H, 6'-H), 6.50 (s, 1H, 8-H), 6.45 (dd, J=8.6, 4.2 Hz, 2H, 2'',6''-H), 5.99 and 5.97 (s and s, 2H, OCH$_2$O), 5.26 (s, 1H, 2'-H), 4.53 (dd, 1H, 11-H), 4.52 (brs, 1H, 4-H), 4.26 (d, J=5.4 Hz, 1H, 1-H), 4.10 (dd, 1H, 11-H), 3.83 (s, 3H, 5'-OCH$_3$), 3.32 (dd, J=14.0, 5.6 Hz, 1H, 2-H), 2.98 (m, 1H, 3-H), IR (KBr) 3380, 1760, 1685, 1650, 1620, 1550, 1495 and 1475; FAB MS m/3 (relative intensity) 478 (M+1)+.

EXAMPLE 44

3',4'-Didemethoxy-3',4'-dioxo-4β-(4''-nitroanilino)-4-desoxypodophyllotoxin mp 234°–236° C. (dec), crystals from ether; $^1$H NMR (CDCl$_3$) δ 8.14 (d, J=9.1 Hz, 2H, 3'',5''-H), 6.70 (s, 1H, 5-H), 6.56 (d, J=9.1 Hz, 2H, 2'',641 -H), 6.53 (s, 1H, 8-H), 6.50 (s, 1H, 6'-H), 6.00 and 5.98 (s and s, 2H, OCH$_2$O), 5.25 (s, 1H, 2'-H), 4.78 (dd, J=6.7, 4.0 Hz, 1H, 4-H), 4.56 (dd, J=10.6, 8.2 Hz, 1H, 11-H), 4.54 (d, 1H, NH), 4.29 (d, J=5.6 Hz, 1H, 1-H), 3.98 (dd, J=10.6, 9.1 Hz, 1H, 11-H), 3.83 (s, 3H, 5-OCH$_3$), 3.25 (dd, J=14.2, 5.6 Hz, 1H, 2-H), 3.06 (m, 1H, 3-H), IR (KBr) 3360, 1760, 1685, 1650, 1615, 1590, 1550, 1492 and 1475 cm$^{-1}$; FAB MS m/3 (relative intensity) 505 (M+1)+.

EXAMPLE 45

3',4'-Didemethoxy-3',4'-dioxo-4β-[(4''-ethoxycarbonyl)anilino]-4-desoxypodophyllotoxin mp 205°–208° C. (dec), crystals from ether; $^1$H NMR (CDCl$_3$) δ 7.92 (d, J=8.6 Hz, 2H, 3'',5''-H), 6.71 (s, 1H, 5-H), 6.52 (d, J=8.6 Hz, 2H, 2'',6''-H), 6.51 (s, 1H, 8-H), 6.50 (s, 1H, 6'-H), 5.99 and 5.97 (s and s, 2H, OCH$_2$O), 5.26 (s, 1H, 2'-H), 4.72 (brs, 1H, 4-H), 4.54 (dd, 1H, 11-H), 4.32 (9, J=7.2 Hz, 2H, 4''-CO$_2$C$\underline{H}_2$CH$_3$), 4.28 (d, J=5.2 Hz, 1H, 1-H), 3.98 (dd, 1H, 11-H), 3.83 (s, 3H, 5'-OCH$_3$), 3.28 (dd, J=14.1, 5.5 Hz, 1H, 2-H), 3.02 (m, 1H, 3-H), 1.36 (t, J=7.2 Hz, 3H, 4''-CO$_2$CH$_2$C$\underline{H}_3$); FAB MS m/3 (relative intensity) 532 (M+1)+.

ISOLATION OF HUMAN DNA TOPOISOMERASE II

Human DNA topoisomerase II was isolated from peripheral blast cells of a patient with acute leukemia. The isolation procedure is described in Thurston, L., Imakura, Y., Haruna, M., Li, Z. C., Liu, S. Y., and Lee, K. H., *J. Med. Chem.*, 31, COMPLETE (1988) and is a partial combination of the procedure described in Goto, T., Laiapia, P. and Wang, J., *J. Biol. Chem.*, 259, 10422 (1984) and Halligan, B., Edwards, K., and Liu, L., *J. Biol. Chem.*, 260, 2475 (1985) which are herein specifically incorporated by reference.

PREPARATIONS OF DRUGS

Drugs were dissolved in Me$_2$SO at a concentration of 20 mM as the stock solution and diluted before use with water to the desired concentration of each drug.

DNA TOPOISOMERASE II ASSAY

The P4 unknotting reaction was a modification of the procedure described by Hseih, T., *J. Biol. Chem.*, 258, 8413 (1985), which is herein specifically incorporated by reference.

The reaction mixture (20 μL), which contained 50 mM HEPES, pH 7.0, 50 mM KCl, 100 mM NaCl, 0.1 mM EDTA, 10 mM MgCl$_2$, 1.0 mM ATP, 50 μg/mL bovine serum albumin, 0.4 μg P4knotted DNA, and enzyme, was incubated with or without drugs.

The reaction mixture was incubated at 37° C. for 30 min and terminated by adding 5.0 μl of a stop solution (2% sodium dodecyl sulfate, 20% glycerol, 0.05% bromophenol blue). These samples were loaded onto a 1% agarose gel and electrophoresed at 55 V overnight with an electrophoresis buffer that contained 90 mM Tris-boric acid, pH 8.3, and 2.5 mM EDTA. At completion, the gel was stained in 0.5 μg/mL of ethidium bromide. Then a photograph was taken of the DNA bands visualized with fluorescence induced by a long-wavelength UV lamp. The data reported in Table 1 reflect a 100 μM drug concentration.

K-SDS PRECIPITATION ASSAY FOR PROTEIN-DNA COMPLEXES

The intracellular formation of covalent topoisomerase II-DNA complexes was quantitated using the potassium SDS precipitation assay, a procedure adapted from the method described in Rowe, T. C., Chen, G. L., Hsiang, Y. H., and Liu, L., *Cancer Res.*, 46, 2021 (1986) (hereinafter Rowe et al.), which is herein specifically incorporated by reference. KB ATCC cells were prelabeled with 0.05 mCi/ml $^{14}$C-thymidine (specific activity 50.5 mCi/mmol) for 18 hr. A final concentration of 5×10$^5$ cells/sample were treated with 10 μM of the drugs at 37° C. for 1 hr and proceeded according to the procedure described by Rowe et al. to detect the protein linked DNA levels.

It will be apparent to those skilled in the art that various modifications and variations can be made in the processes and products of the present invention. Thus, it is intended that the present invention cover the modifications and variations of this invention provided that they come within the scope of the appended claims and their equivalents.

TABLE 1

Biological Evaluation of 4β-substituted benzylamino Podophphylloyoxins

| example | R | Cytotoxicity[a] ID$_{50}$ KB(μM) | Inhibition of DNA Topo-isomerase II Activity[b] ID$_{50}$ | Cellular Protein-DNA Complex Formation (%) 10 μM |
|---|---|---|---|---|
| etoposide | (sugar group) | 0.20 | 50 | 100 |
| 3 | —NH—CH$_2$—C$_6$H$_5$ | 2.20 | 25 | 180 |
| 4 | —NHCH$_2$—C$_6$H$_4$—NO$_2$ (p) | 0.40 | 50 | 215 |
| 5 | —NHCH$_2$—C$_6$H$_4$—NO$_2$ (m) | <0.40 | 25 | 129 |
| 6 | —NHCH$_2$—C$_6$H$_4$—NO$_2$ (o) | 1.80 | 50 | 143 |
| 7 | —NHCH$_2$—C$_6$H$_4$—F (o) | 1.90 | 100 | 125 |
| 8 | —NHCH$_2$—C$_6$H$_4$—F (m) | 3.00 | 25 | 215 |
| 9 | —NHCH$_2$—C$_6$H$_4$—F (p) | >4.00 | 50 | 168 |
| 10 | —NHCH$_2$—C$_6$H$_4$—CN (m) | <0.40 | 25 | 224 |

TABLE 1-continued

Biological Evaluation of 4β-substituted benzylamino Podophphylloyoxins

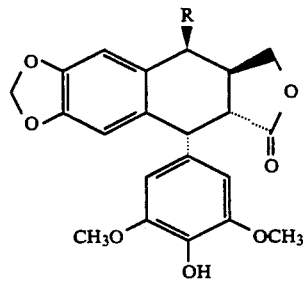

| example | R | Cytotoxicity[a] ID$_{50}$ KB(μM) | Inhibition of DNA Topoisomerase II Activity[b] ID$_{50}$ | Cellular Protein-DNA Complex Formation (%) 10 μM |
|---|---|---|---|---|
| 11 | —NH—CH$_2$—C$_6$H$_4$—CN | <0.40 | 25 | 283 |
| 12 | —NHCH$_2$—C$_6$H$_3$(OCH$_3$)$_2$ (3,5) | 1.70 | 100 | 143 |
| 13 | —NHCH$_2$—C$_6$H$_4$—NH$_2$ (3) | <0.40 | 25 | 190 |
| 14 | —NHCH$_2$—C$_6$H$_4$—NH$_2$ (2) | <0.40 | 25 | 183 |

[a]ID$_{50}$ was the concentration of drug which affords 50% reduction in cell number after three day incubation.

[b]Each compound was examined with three concentrations at 25, 50, and 100 μM. The ID$_{50}$ value was established based on the degree of inhibition at these three concentrations.

TABLE 2

Biological Evaluation of 4β-substituted Anilino Derivatives of 3',4'-O-Didemethylpodophyllotoxin

| example | R | Cytotoxicity[a] ID$_{50}$ KB(μM) | Inhibition of DNA Topo-isomerase II Activity[b] ID$_{50}$ | Cellular Protein-DNA Complex Formation (%) 10 μM |
|---|---|---|---|---|
| etoposide | (sugar moiety) | 0.20 | 50 | 100 |
| 17 | —NH—C$_6$H$_5$ | 1.7 | 25 | 128 |
| 18 | —NH—C$_6$H$_4$—F | 3.0 | 10 | 117 |
| 19 | —NH—C$_6$H$_4$—OH | 1.6 | 10 | 105 |
| 20 | —NH—C$_6$H$_3$(OCH$_2$CH$_2$O) | 2.3 | 10 | 119 |
| 21 | —NH—C$_6$H$_4$—CO$_2$CH$_3$ | 1.9 | 1.0 | 175 |
| 22 | —NH—C$_6$H$_4$—CN | 1.5 | 10 | 146 |
| 23 | —NH—C$_6$H$_4$—NO$_2$ | 1.3 | 10 | 200 |

[a]ID$_{50}$ was the concentration of drug which affords 50% reduction in cell number after three day incubation.
[b]Each compound was examined with three concentrations at 10, 25, 50, and 100 μM. The ID$_{50}$ value was established based on the degree of inhibition at these three concentrations.

TABLE 3

Biological Evaluation of 4β-sbustituted anilino derivatives of 6.7-O-dimethylene-4'-O-demethylpodophyllotoxin

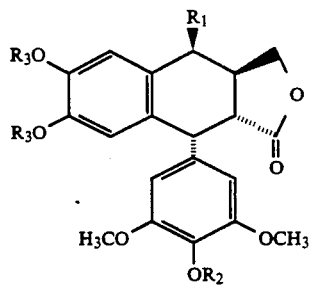

| example | $R_1$ | $R_2$ | $R_3$ | Cytotoxicity[a] $ID_{50}$ KB (uM) | Inhibition of DNA Topo-isomerase II Activity[b] $ID_{50}$ | Cellular Protein-DNA Complex (%) 20 μM |
|---|---|---|---|---|---|---|
| Etoposide | | H | $CH_2$ | 0.20 | 50 | 100 |
| 26 | —NH—C₆H₅ | H | H | >1.00 | 25 | 84 |
| 27 | —NH—C₆H₄—$NO_2$ | H | H | 0.76 | 20 | 99 |
| 28 | —NH—C₆H₄—$CO_2C_2H_5$ | H | H | 0.78 | 20 | 138 |
| 29 | —NH—C₆H₄—CN | H | H | 1.00 | 20 | 62 |
| 30 | —NH—C₆H₄—F | H | H | >1.00 | 25 | 52 |
| 31 | —NH—C₆H₄—F | H | $CH_3$ | 0.40 | 50 | 108 |
| 32 | —NH—C₆H₄—CN | H | $CH_3$ | <0.40 | 50 | 125 |
| 33 | —NH—C₆H₄—$CO_2C_2H_5$ | H | $CH_3$ | <0.40 | 100 | 127 |

[a]$ID_{50}$ was the concentration of drug which affords 50% reduction in cell number after three day incubation.
[b]Each compound was examined with three concentrations at 20, 25, 50, and 100 μM. The $ID_{50}$ value was established based on the degree of inhibition at these three concentrations.

TABLE 4

Biological Evaluation of 4β-Amide Derivatives of 4'-O-Demethylpodophyllotoxin

| example | R | Cytotoxicity[a] ID$_{50}$ KB(μM) | Inhibition of DNA Topo-isomerase II Activity[b] ID$_{50}$ | Cellular Protein-DNA Complex Formation (%) 20 |
|---|---|---|---|---|
| etoposide | (sugar moiety: H$_3$C, O, HO, OH) | 0.20 | 50 | 100 |
| 34 | —NHCO—C$_6$H$_5$ | 0.64 | >50 | 177 |
| 35 | —NHCO—C$_6$H$_4$-OH (ortho) | <1.00 | 50 | 160 |
| 36 | —NHCO—C$_6$H$_4$-F (para) | 0.34 | 25 | 117 |
| 37 | —NHCO—C$_6$H$_4$-OCOCH$_3$ | 0.61 | 25 | 137 |
| 38 | —NHCO—C$_6$H$_4$-COCH$_3$ | 1.00 | 50 | 124 |
| 39 | —NHCO—C$_6$H$_4$-CN (meta) | 1.00 | 50 | 149 |
| 40 | —NHCO—C$_6$H$_4$-CN (para) | 0.10 | 25 | 159 |
| 41 | —NHCO—C$_6$H$_4$-NO$_2$ | 0.33 | 10 | 86 |

TABLE 4-continued

Biological Evaluation of 4β-Amide Derivatives of 4'-O-Demethylpodophyllotoxin

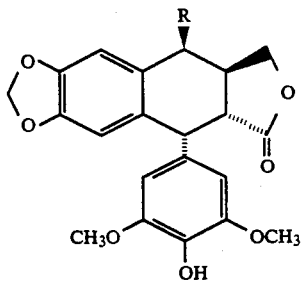

| example | R | Cytotoxicity[a] ID$_{50}$ KB(μM) | Inhibition of DNA Topo-isomerase II Activity[b] ID$_{50}$ | Cellular Protein-DNA Complex Formation (%) 20 |
|---|---|---|---|---|
| 42 | —NHCO—⟨phenyl⟩—NH$_2$ | 0.42 | 25 | 149 |

[a]ID$_{50}$ was the concentration of drug which affords 50% reduction in cell number after three day incubation.
[b]Each compound was examined with three concentrations at 10, 25, 50, and 100 μM. The ID$_{50}$ value was established based on the degree of inhibition at these three concentrations.

TABLE 5

Biological Evaluation of 4β-substituted Anilino Derivatives of 3',4'-Didemethoxy-3',4'-dioxo-4-desoxypodophyllotoxin

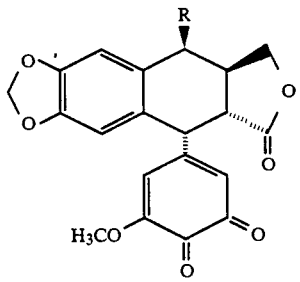

| example | R | Cytotoxicity[a] ID$_{50}$ KB(μM) | Inhibition of DNA Topo-isomerase II Activity[b] ID$_{50}$ | Cellular Protein-DNA Complex Formation (%) 20 μM |
|---|---|---|---|---|
| etoposide | (sugar structure) | 0.20 | 50 | 100 |
| 43 | —NH—⟨phenyl⟩—F | >2.1 | 25 | 92 |
| 44 | —NH—⟨phenyl⟩—NO$_2$ | 1.5 | 10 | 128 |

TABLE 5-continued

Biological Evaluation of 4β-substituted Anilino Derivatives of 3',4'-Didemethoxy-3',4'-dioxo-4-desoxypodophyllotoxin

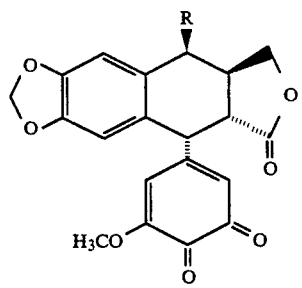

| example | R | Cytotoxicity[a] $ID_{50}$ KB(μM) | Inhibition of DNA Topo- isomerase II Activity[b] $ID_{50}$ | Cellular Protein-DNA Complex Formation (%) 20 μM |
|---|---|---|---|---|
| 45 | —NH—C$_6$H$_4$—CO$_2$C$_2$H$_5$ | 1.1 | 25 | 110 |

[a]$ID_{50}$ was the concentration of drug which affords 50% reduction in cell number after three day incubation.
[b]Each compound was examined with three concentrations at 10, 25, 50, and 100 μM. The $ID_{50}$ value was established based on the degree of inhibition at these three concentrations.

SCHEME 1

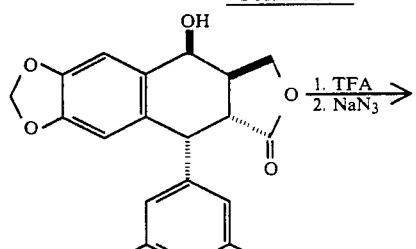

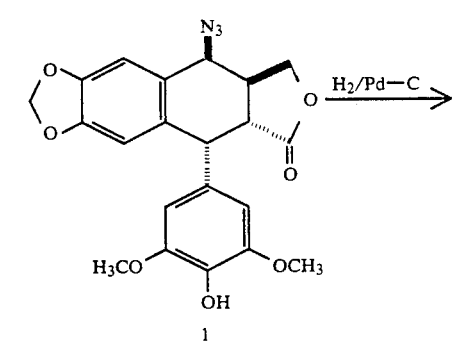

-continued
SCHEME 1

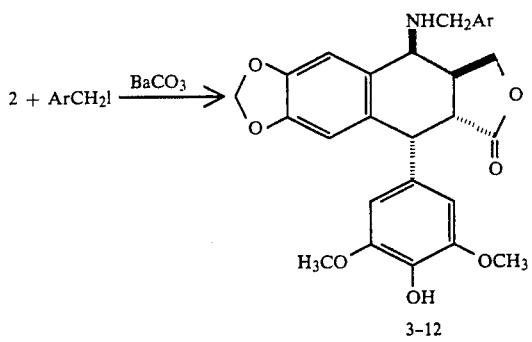

5-6 $\xrightarrow{SnCl_2}$ 13-14

SCHEME 2

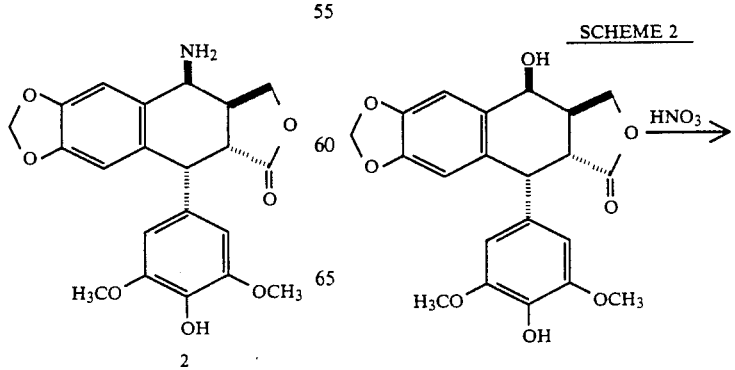

-continued
SCHEME 2
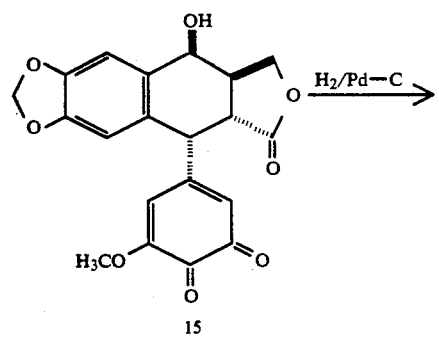
15
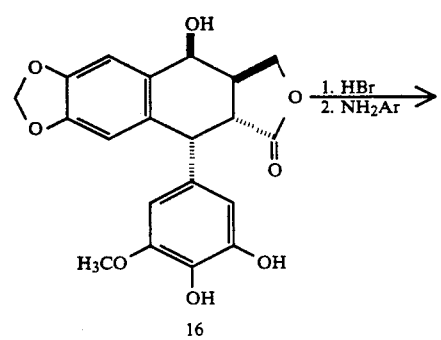
16
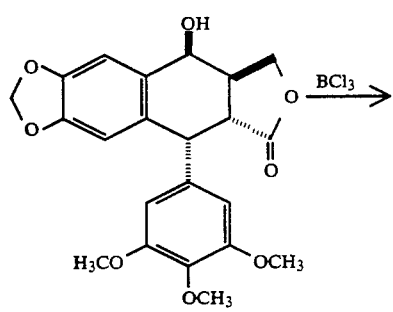
SCHEME 3
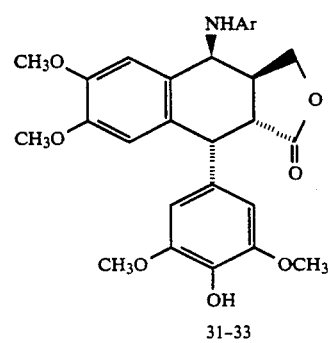
-continued
SCHEME 3
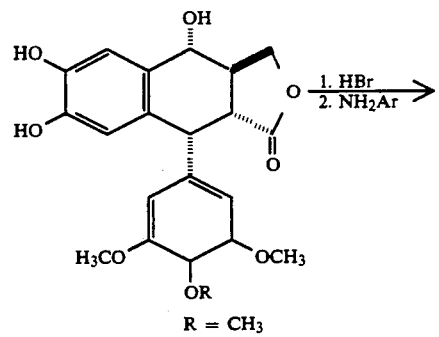
R = CH₃
R = H
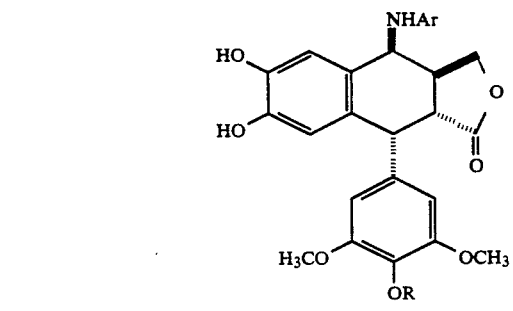
R
SCHEME 4
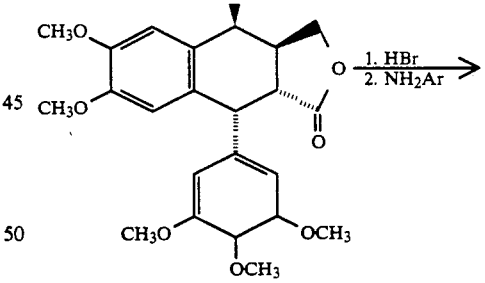
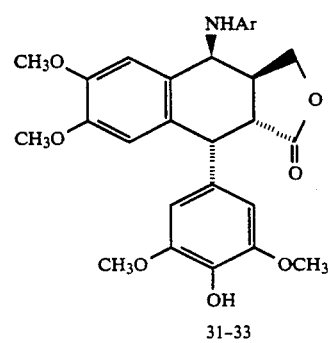
31–33

SCHEME 5

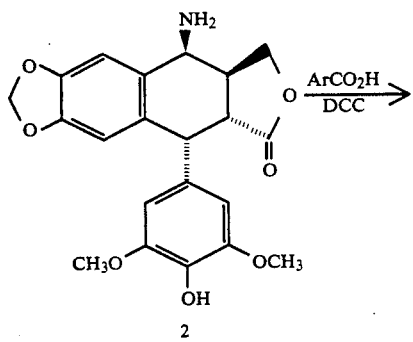

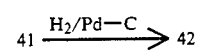

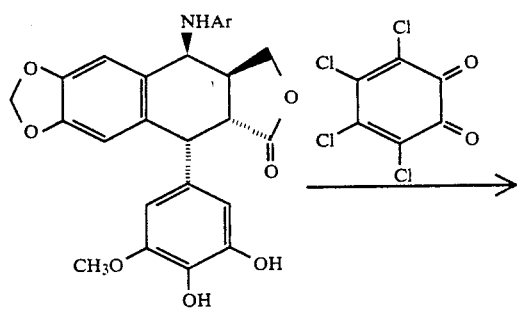

SCHEME 6

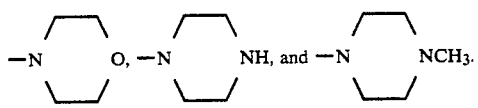

-continued
SCHEME 6

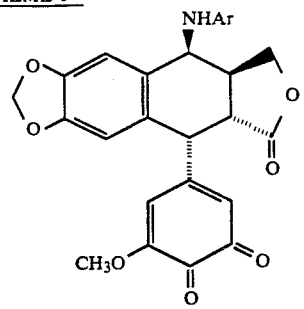

What is claimed is:

1. A compound having the formula II:

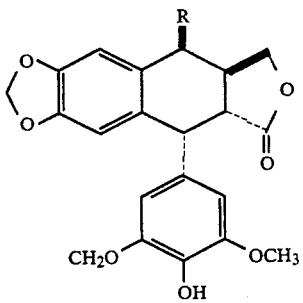

wherein R is

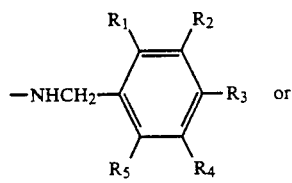

wherein $R_1$, $R_2$, $R_3$, $R_4$ and $R_5$ are each independently selected from H, $CH_3$, $C_2H_5$, $C_3H_7$, i—$C_3H_7$, $C_4H_9$, $CF_3$, $OCH_3$, $OC_2H_5$, $OC_3H_7$, $OC_4H_9$, O—i—$C_3H_7$, O—i—$C_4H_9$, —$OCH_2O$—, —$OCH_2CH_2O$—, $CH_2OH$, $C_2H_4OH$, $CH_2Cl$ $C_2H_4Cl$, $CH_2F$, $C_2H_4F$, $CH_2OCH_3$, $COCH_3$, $COC_2H_5$, $CO_2CH_3$, $CO_2C_2H_5$, $NO_2$, $NH_2$, $NH_2$·HCl, $NH_2$·HAc, $NH_2·\tfrac{1}{2}H_2SO_4$, $NH_2·\tfrac{1}{3}H_3PO_4$, $N(CH_3)_2$, $N(C_2H_5)_2$, OH, CN, $N_3$, $SO_2H$, $SO_2NH_2$, $SO_2Cl$, phenyl, phenoxy, anilinyl, cyclohexyl, piperidine, $-N\!\!\bigcirc\!\!O$, $-N\!\!\bigcirc\!\!NH$, and $-N\!\!\bigcirc\!\!NCH_3$.

2. A compound according to claim 1, wherein R is selected from benzylamino, 4"-nitrobenzylamino, 3"-nitrobenzylamino, 2"-nitrobenzylamino, 2"-fluorobenzylamino, 3"-fluorobenzylamino, 4"-fluorobenzylamino, 3"-cyanobenzylamino, 4"-cyanobenzylamino, 3",5"-dimethoxybenzylamino, 3"-aminobenzylamino, and 2"-aminobenzylamino.

3. A compound according to claim 1, wherein R is selected from 3"-fluorobenzylamino, 3"-cyanobenzylamino and 4"-cyanobenzylamino.

4. A pharmaceutical composition comprising a compound as claimed in claim 1 and a pharmaceutically acceptable carrier.

* * * * *